US012806213B2

(12) United States Patent
Qian et al.

(10) Patent No.: US 12,806,213 B2
(45) Date of Patent: Nov. 24, 2026

(54) USE OF ANDROGEN RECEPTOR-MEDIATED MECHANISMS IN THE TREATMENT OF ACUTE MYELOID LEUKEMIA

(71) Applicant: The Penn State Research Foundation, University Park, PA (US)

(72) Inventors: Fenghua Qian, University Park, PA (US); Kumble Sandeep Prabhu, University Park, PA (US); Robert F. Paulson, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 230 days.

(21) Appl. No.: 18/858,300

(22) PCT Filed: Apr. 18, 2023

(86) PCT No.: PCT/US2023/065881
§ 371 (c)(1),
(2) Date: Oct. 18, 2024

(87) PCT Pub. No.: WO2023/205629
PCT Pub. Date: Oct. 26, 2023

(65) Prior Publication Data

US 2025/0268920 A1 Aug. 28, 2025

Related U.S. Application Data

(60) Provisional application No. 63/332,943, filed on Apr. 20, 2022.

(51) Int. Cl.

| | |
|---|---|
| ***A61K 31/58*** | (2006.01) |
| ***A61K 31/4439*** | (2006.01) |
| ***A61P 35/02*** | (2006.01) |

(52) U.S. Cl.
CPC .......... *A61K 31/58* (2013.01); *A61K 31/4439* (2013.01); *A61P 35/02* (2018.01)

(58) Field of Classification Search
CPC ...................................................... A61K 31/58
See application file for complete search history.

(56) References Cited

U.S. PATENT DOCUMENTS

| | | | |
|---|---|---|---|
| 2007/0149571 | A1 | 6/2007 | Stein et al. |
| 2021/0033613 | A1 | 2/2021 | Averback |
| 2021/0161837 | A1 | 6/2021 | Chen et al. |

FOREIGN PATENT DOCUMENTS

| | | | |
|---|---|---|---|
| WO | 2016/130816 | A1 | 8/2016 |
| WO | 2023/039125 | A1 | 3/2023 |

OTHER PUBLICATIONS

Cheng, P-T., et al., Abstract A12: Androgen receptor inhibition is involved in Finasteride-reduced AML cell proliferation, Blood Cancer Discovery, May 1, 2023, vol. 4, No. 3, 4 pages.

*Primary Examiner* — Golam M Shameem
(74) *Attorney, Agent, or Firm* — Hodgson Russ LLP

(57) ABSTRACT

Provided is a method for treating a blood cancer in an individual in need thereof by administrating to the individual an agent that inhibits activity or expression of one or more enzymes that participate in synthesis of either or both dihydrotestosterone (DHT) or androgen receptor (AR), or an antagonist AR, or a combination of an agent and the antagonist. The methods are shown in connection with acute myeloid leukemia (AML).

11 Claims, 41 Drawing Sheets

| Donor | Recipient | Severity of AML |
|---|---|---|
| Female | Female | +++ |
| Female | Male | ++++ |
| Male | Female | + |
| Male | Male | ++ |

FIG. 9A
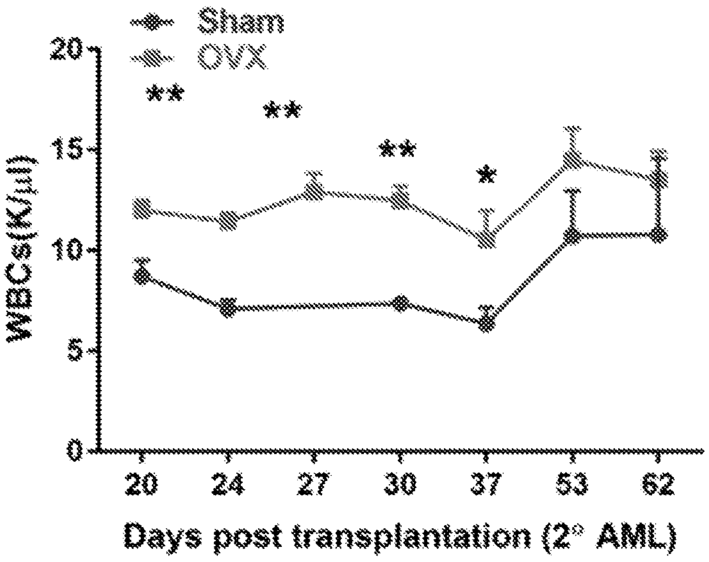
FIG. 9B
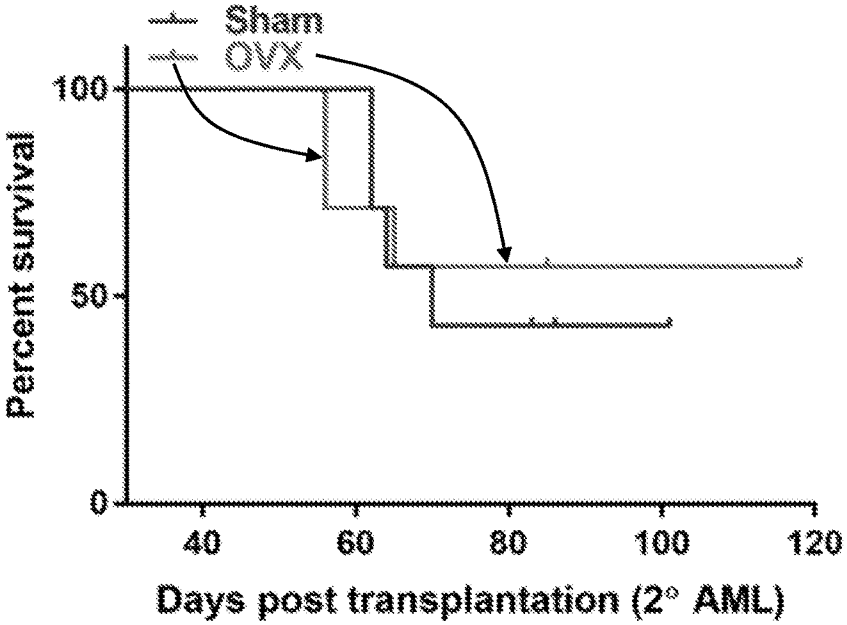
FIG. 9C
| | Sham | OVX |
|---|---|---|
| Development of leukemia | 4/7 | 3/7 |
| Uterine prolap se | 3/7 (not leukemic mice) | 0/7 |
| Spinal tumor | 1/7 (not leukemic mice) | 1/7 (not leukemic mice) |
| Survival till endpoint | 0/7 | 3/7 |

USE OF ANDROGEN RECEPTOR-MEDIATED MECHANISMS IN THE TREATMENT OF ACUTE MYELOID LEUKEMIA

CROSS REFERENCE TO RELATED APPLICATION

This application claims priority to U.S. provisional patent application No. 63/332,943, filed Apr. 20, 2022, the entire disclosure of which is incorporated herein by reference.

STATEMENT REGARDING FEDERALLY SPONSORED RESEARCH OR DEVELOPMENT

This invention was made with government support under Grant No. NI22HFPXXXXXG019 awarded by the United States Department of Agriculture. The Government has certain rights in the invention.

RELATED INFORMATION

Relapse of acute myeloid leukemia (AML) remains a significant concern due to persistent leukemia cells that are typically not targeted by existing therapies. This is partly due to the leukemia-initiating cells (LICs) that are resistant to current therapeutic interventions leading to the expansion and relapse of leukemia. The mainline therapy for AML has generally remained the same for many years, with a need for new therapies to target LICs. There is accordingly an unmet need for improved approaches to treating AML and other leukemias. The present disclosure is pertinent to this need.

BRIEF SUMMARY

Based on sexual dimorphic effects in terms of severity of the disease in humans as well as a rodent model of AML, this disclosure provides an analysis of the role of androgen receptor (AR) in therapy for AML to elucidate mechanisms underlying the effects of steroid hormones on disease progression to describe essential processes that mediate gender-specific susceptibility, and provide new treatments for AML and other blood cancers. The disclosure includes an analysis of the progression of AML by dissecting the source of leukemia cells from female and male donor mice upon reciprocal transplantation into female or male recipients for each donor set. To address the role of AR, the disclosure demonstrates use of two United States Food and Drug Administration (USFDA) approved drugs, ARN-509 (Erleada®) and Finasteride (Proscar®), which antagonize AR or inhibit the pathway that produces the high-affinity endogenous ligand dihydrotestosterone (DHT) for AR, respectively. Antagonism of AR or decreasing the levels of the endogenous ligand(s) (DHT) of AR significantly improved the prognosis in the murine model of AML in all sexes of mice with a profound effect on leukemia cells derived from female and male mice. The disclosure thus provides methods for treating AML by targeting a newly described pathway involving AR and the generation of its endogenous ligands.

BRIEF DESCRIPTION OF THE FIGURES

FIG. 9A, FIG. 9B, and FIG. 9C show that ovariectomy of female recipient mice does not change the outcome of AML.

DETAILED DESCRIPTION

Figure 1A:
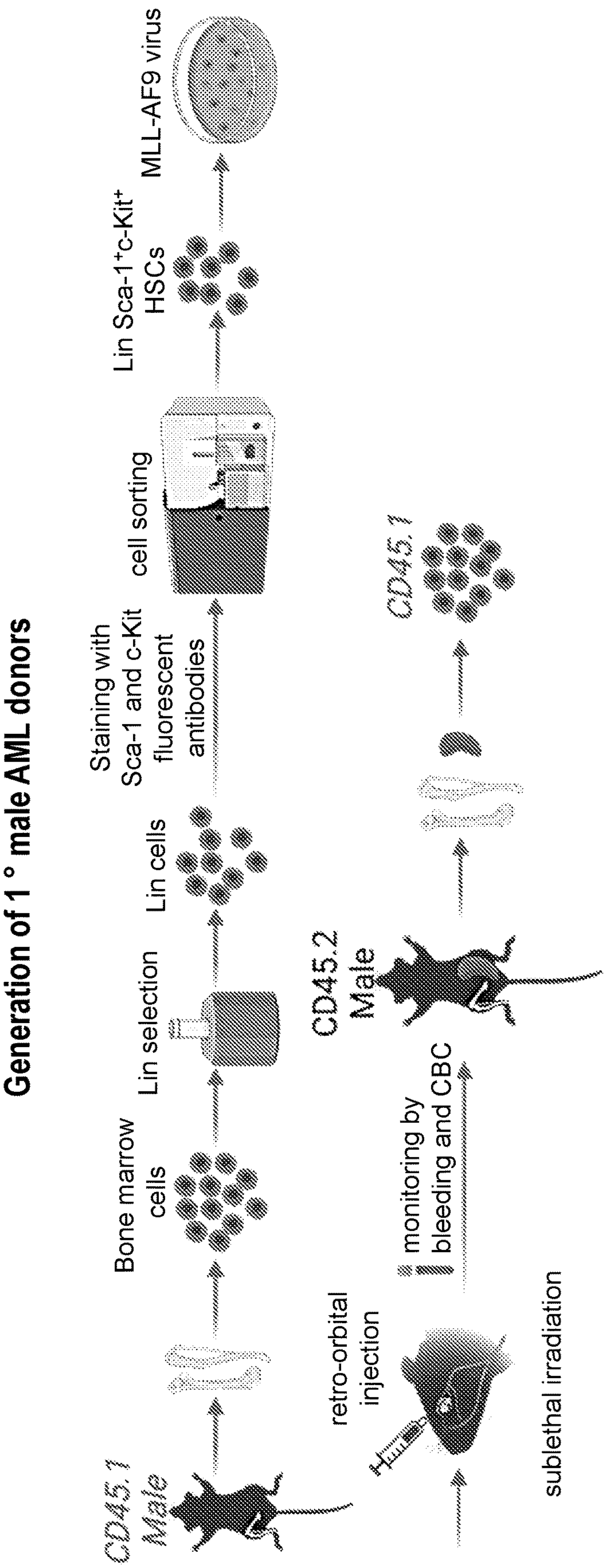
FIG. 1A, FIG. 1B, and FIG. 1C depict generation of primary male and female AML donor cells and results from leukemic cells that infiltrated and populated in bone marrow, spleen, and liver of recipients.

Unless defined otherwise, all technical and scientific terms used herein have the same meaning as commonly understood by one of ordinary skill in the art to which this invention belongs.

Every numerical range given throughout this specification includes its upper and lower values, as well as every narrower numerical range that falls within it, as if such narrower numerical ranges were all expressly written herein. As used herein, the singular forms "a" "and" and "the" include plural referents unless the context clearly dictates otherwise.

This disclosure provides methods for prophylaxis and/or therapy for blood cancer. The disclosure also includes the described mouse models of blood cancer.

In general, a method provided by the disclosure comprises administering one or more agents to an individual who is suspected of having or has been diagnosed with a blood cancer to thereby treat the blood cancer. The one or more agents are selected from i) agents that inhibit activity or expression of one or more enzymes that participate in synthesis of either or both dihydrotestosterone (DHT) or androgen receptor, or ii) antagonists of androgen receptor (AR), or a combination of agents as in i) and ii).

In embodiments, the enzyme that participates in synthesis of DHT is 3α-oxidoreductase or 5-α reductase, including any isoforms of 3α-oxidoreductase and 5-α reductase. The disclosure also includes inhibiting the expression or function of PI3K, AKT, MTORC, or the proteins encoded by those genes, or a combination thereof.

In embodiments, the agent(s) administered to the individual comprises one or more AR antagonists. Suitable AR antagonists are known in the art. In embodiments, the AR antagonist comprises ARN-509 (sold under the trade name Erleada® and also referred to as ARN509 and Apalutamide), Finasteride (sold under the trade name Proscar®), Dutasteride, Apalutamide, Bicalutamide, Enzalutamide, Nilutamide, or a combination thereof.

In embodiments, the agent that inhibits activity or expression of one or more enzymes that participate in synthesis of DHT or AR functions to eliminate or disrupt gene(s) that encode the enzymes or the AR, or inhibits the expression of the enzymes or the AR. In embodiments, the agent inhibits persistence of mRNA encoding one or more of the described enzymes or AR in cytoplasm, or inhibits translation of mRNA that encodes the described enzymes or the AR. In embodiments, the agent comprises an RNAi agent, said agent being any of an antisense oligonucleotide, a microRNA, an shRNA, or a ribozyme. In an embodiment, the agent comprises a CRISPR system, the CRISPR system comprising at least one Cas enzyme and at least one guide RNA that targets one or more genes encoding said one or more enzymes. Any suitable CRISPR system may be used, and include Type I, II, III, IV, or Type V CRISPR systems. The CRISPR or other system described system disrupts or deletes said one or more genes that encode one or more enzymes that participate in the synthesis of DHT and/or the gene that encodes the AR. The CRISPR systems include at least one CRISPR effector protein and a guide RNA targeted to chromosome that encodes a described target. Other site directed nucleases may also be used, as can transposon-based systems. Alternatively, TALEN or zinc finger nucleases may be used.

CRISPR systems, RNAi-mediating agents, and other gene editing systems described above may be administered to an individual or to cells isolated from an individual using any suitable technique. In embodiments, one or more expression vectors are used and may comprise viral vectors. Thus, in embodiments, a viral expression vector is used. Viral expression vectors may be used as naked polynucleotides, or may comprise any of viral particles, including but not limited to defective interfering particles or other replication defective viral constructs, and virus-like particles. In embodiments, the expression vector comprises a modified viral polynucleotide, such as from an adenovirus, a herpesvirus, or a retrovirus. In embodiments, a retroviral vector adapted from a murine Maloney leukemia virus (MLV) or a lentiviral vector may be used, such as a lentiviral vector adapted from human immunodeficiency virus type 1 (HIV-1). In an embodiment, an oncolytic viral vector is used. In alternative embodiments, a recombinant adeno-associated virus (AAV) vector may be used. In certain embodiments, the expression vector is a self-complementary adeno-associated virus (scAAV).

For CRISPR or other targeted nucleases used in gene editing approaches, the disclosure includes isolating cells from an individual and editing the cells to disrupt or delete one or more of the described genes. In embodiments, the cells that are edited are hematopoietic stem cells. In embodiments, the disclosure includes obtaining the described cells from an individual, modifying the cells ex vivo using a CRISPR system or other targeted nuclease system as described herein, and reintroducing the cells or their progeny into the individual for prophylaxis and/or therapy of a blood cancer.

The blood cancer with which the individual is diagnosed or is suspected of having may be any leukemia and thus may be any acute or chronic leukemia. In certain embodiments the leukemia may be acute myeloid leukemia (AML). In embodiments, administration of one or a combination of the described agents inhibits progression of AML, eradicates AML, inhibits or reduces the severity of AML relapse, improves the prognosis of the individual, extends the lifespan of the individual, or a combination thereof. In embodiments, administration of one or a combination of the described agents improves the prognosis of the individual who has AML. In one embodiment, the method comprises selecting an individual diagnosed with AML and administering one or more of the described agents to the individual. In embodiments, the described methods are used to treat a blood cancer in a human individual. In embodiments, the individual in need of treatment does not have any form of prostate cancer. In embodiments, the individual in need of treatment does not have benign prostatic hyperplasia (BPH). In embodiments, the individual in need of the treatment does not have a prostate gland. In embodiments, the individual in need of the treatment is a female human.

In embodiments, an effective amount of one or more described agents is administered to an individual in need thereof. In embodiments, an effective amount is an amount that reduces one or more signs or symptoms of a blood cancer or the severity of the blood cancer. An effective amount may also inhibit or prevent the onset of blood cancer, or prevent or inhibit blood cancer. A precise dosage can be selected by the individual physician in view of the patient to be treated. Dosage and administration can be adjusted to provide sufficient levels of the described agents to maintain the desired effect. Additional factors that may be considered include the severity and type of the blood cancer, stage of the cancer, age, weight, and gender of the patient, desired duration of treatment, method of administration, time and frequency of administration, drug combination(s), reaction sensitivities, and/or tolerance/response to therapy.

The described agents can be administered to an individual in need thereof using any suitable route, examples of which include intravenous, intraperitoneal, and oral routes. One or more of the described agents may be introduced as a single administration or as multiple administrations or may be introduced in a continuous manner over a period of time. For example, the administration(s) can be a pre-specified number of administrations or daily, weekly, or monthly administrations, which may be continuous or intermittent, as may be therapeutically indicated. As revealed by the description below, dosing may be different for male and female patients.

The following Examples are intended to illustrate but not limit the disclosure.

Example 1

Results in this Example are shown in the panels of FIG. 1, and demonstrate generation of primary male and female AML donors. Parenthetical references to panels in this and the following Examples refer to the corresponding figures.

Figure 1B:
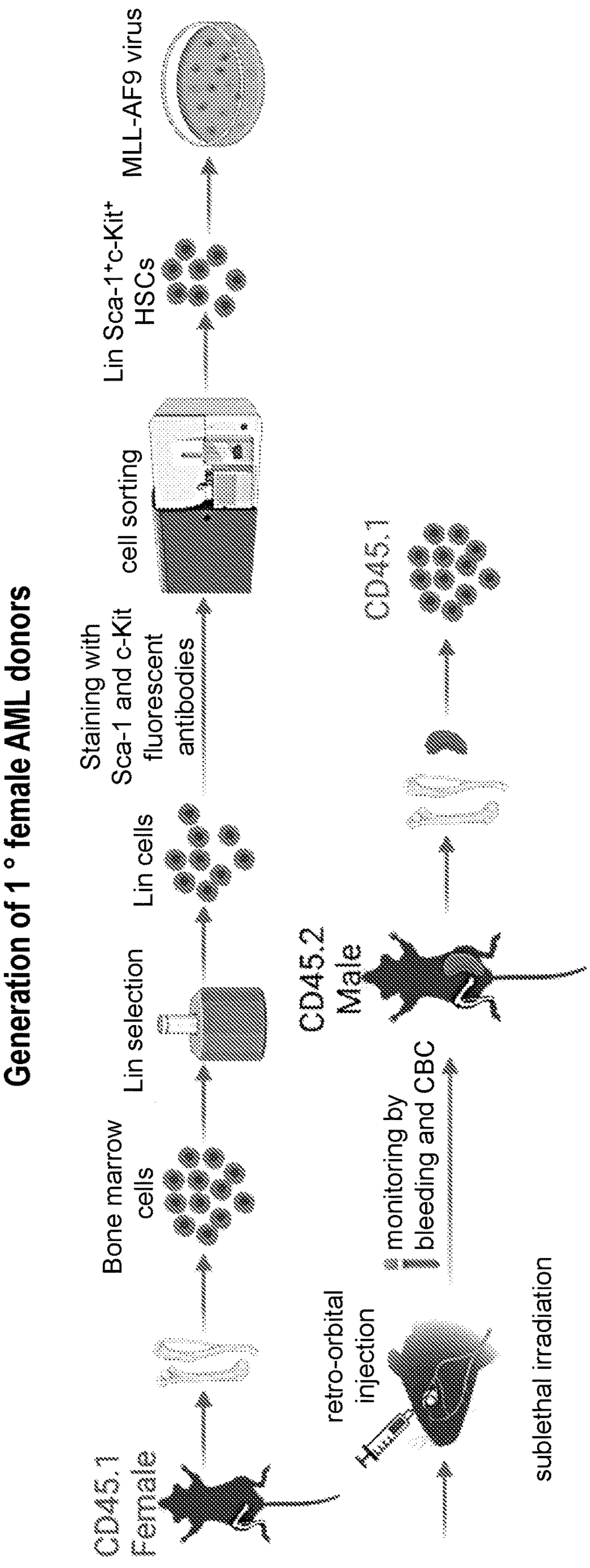
Figure 1C:
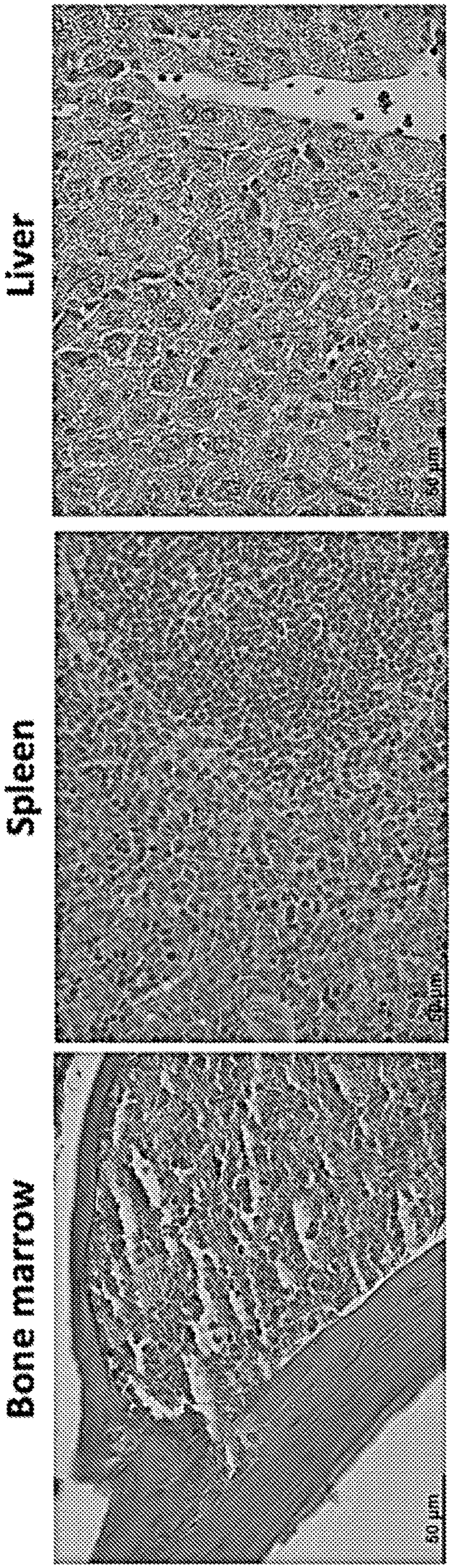

To obtain the results shown in FIG. 1, we isolated bone marrow cells from CD45.1 male mice (FIG. 1A) and CD45.1 female mice (FIG. 1B). Bone marrow cells were applied to hematopoietic stem/progenitor cell isolation using a kit (EasySep™ mouse hematopoietic progenitor cell isolation kit, STEMCELL, Catalog #19856) followed by red blood cell lysis. Lineage negative ($Lin^-$) cells were stained with fluorescent antibodies including Sca-1 and c-Kit and then sent to a Beckman Coulter MoFlo Astrios EQ Cell Sorter for sorting $Sca\text{-}1^+c\text{-}Kit^+$ cells. These cells were cultured in a $CO_2$ incubator at 37° C. in the presence of MLL-AF9 virus (for AML) for six hours and then injected retro-orbitally into CD45.2 recipient mice. Recipients received sublethal irradiation (475 rads) and $1.5\sim3.5\times10^5$ $Lin^-Sca\text{-}1^+c\text{-}Kit^+$ hematopoietic stem cells (HSCs). Mice were monitored for complete cell counts by bleeding retro-orbitally one month post transplantation. Retro-orbital bleeding was performed weekly. When primary recipients showed symptoms and signs of AML such as leukocytosis (WBC>50 K/μL) and hepatosplenomegaly, the mice were euthanized and leukemic cells were isolated from spleen and bone marrow, followed by flow cytometric analysis of $CD45.1^+$ cells. The results showed that $CD45.1^+$ leukemic cells infiltrated and populated in the bone marrow, spleen, and liver of recipients (FIG. 1C), and the high frequency of leukemic cells (up to 95%) in both sites indicated the successful generation of AML donors of male and female sources.

Example 2

Figure 2A:
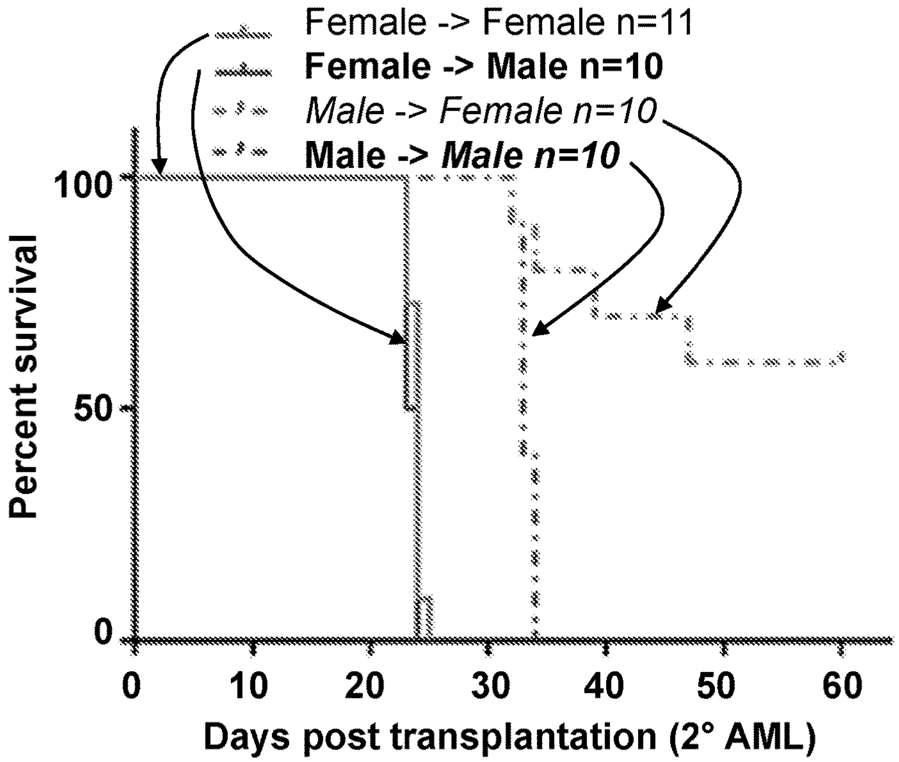
FIG. 2A, FIG. 2B, FIG. 2C, and FIG. 2D demonstrate survival analysis in secondary transplantation of female and male AML cells into females and males.
Figure 2B:
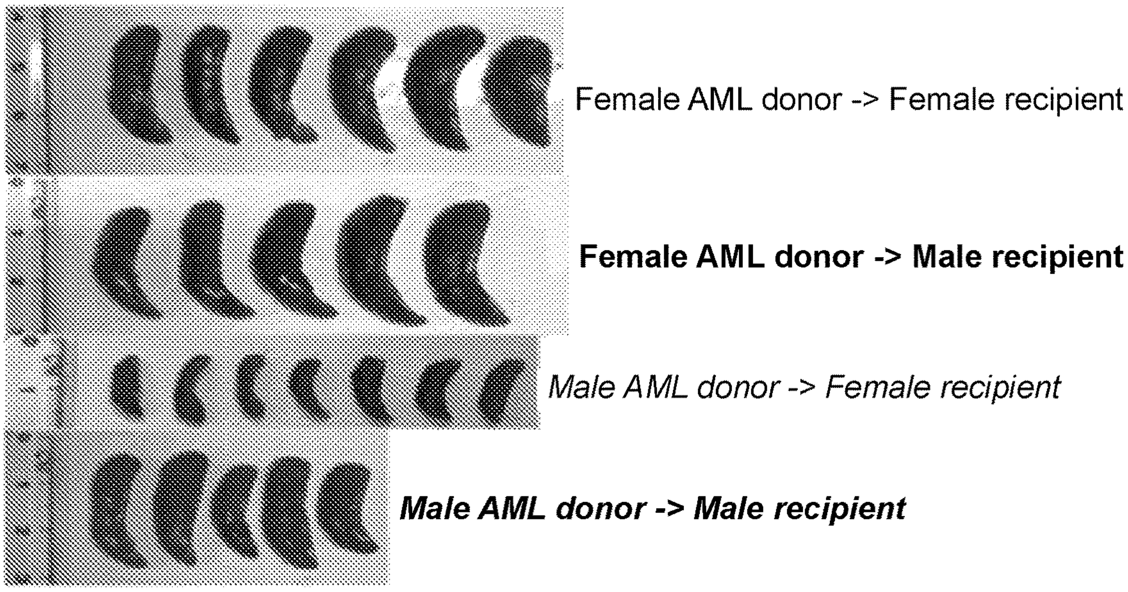
Figures 2C, 2D:
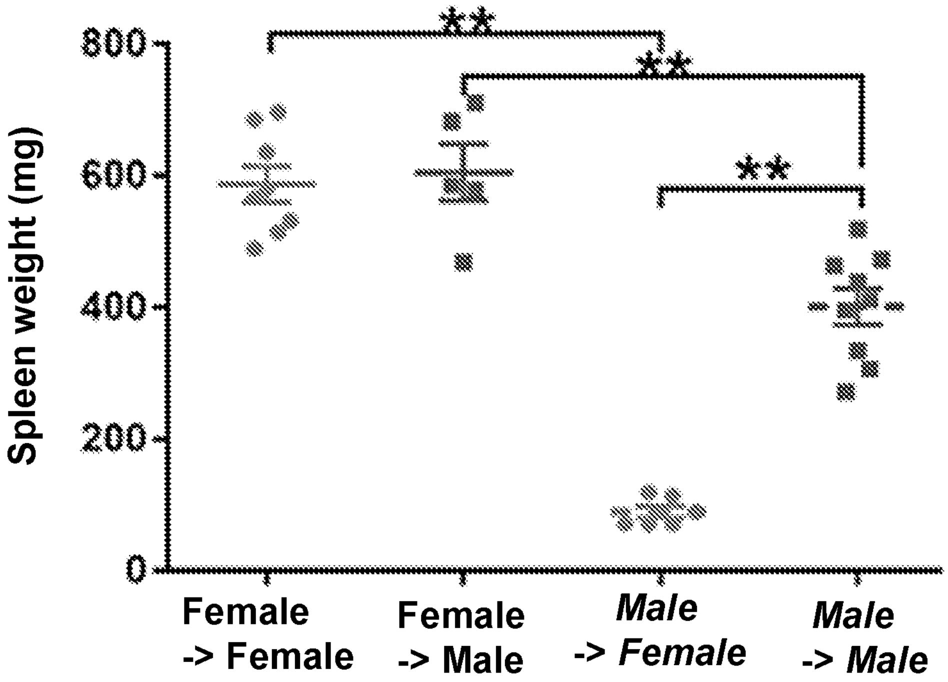

The results of this Example are represented in FIGS. 2A, 2B, 2C and 2D, and show a survival analysis in secondary transplantation of female and male AML cells into females and males. To obtain the results, primary (1°) female or 1° male AML donor cells (generated according to FIGS. 1A and 1B) were injected retro-orbitally into both female and male wild-type recipients. (FIG. 2A). Follow-up of the survival of recipients up to 60 days post transplantation showed that female AML donor cells-transplanted recipients had the most severe disease and shortest survival and there was no significant difference between female and male recipients. Male AML donor cells could only generate the disease in male recipients, but not in female recipients, and male AML donor cells-transplanted male recipients that had improved survival compared to female AML donor cells-transplanted recipients, indicating that female AML donor cells were much more aggressive than male AML donor cells. In addition, increased survival in female recipients transplanted with male AML donors indicates that female recipients had protective effect(s) compared to their male counterparts, and such effects were shown in female AML donor-transplanted female recipients by the increased aggressiveness of female AML donor cells. (FIG. 2B) (FIG. 2C) Consistently, splenomegaly also supported the described approach. (FIG. 2D) This Example therefore demonstrates that: 1) Female AML donor cells are more aggressive than male AML donor cells; and 2) Female recipients have potential protective mechanism(s) that lead to an improved survival compared to their male counterparts.

Example 3

Figure 3A:
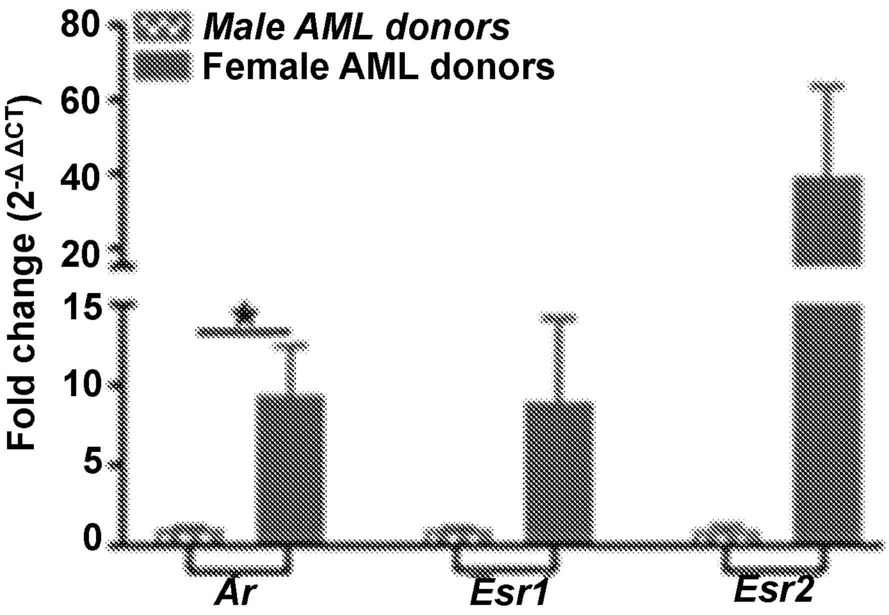
FIG. 3A, FIG. 3B, FIG. 3C, and FIG. 3D demonstrate analysis of the expression of androgen receptor and estrogen receptors on female and male AML cells.
Figure 3B:
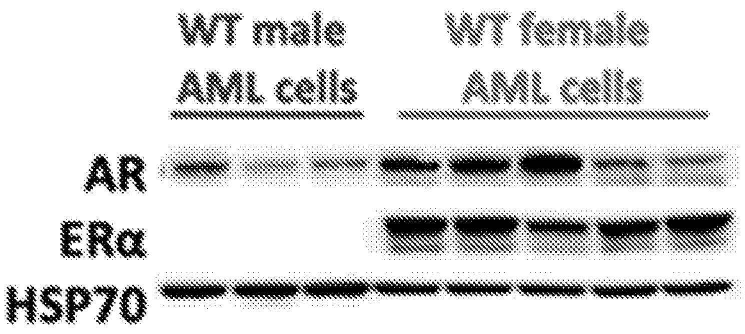
Figure 3C:
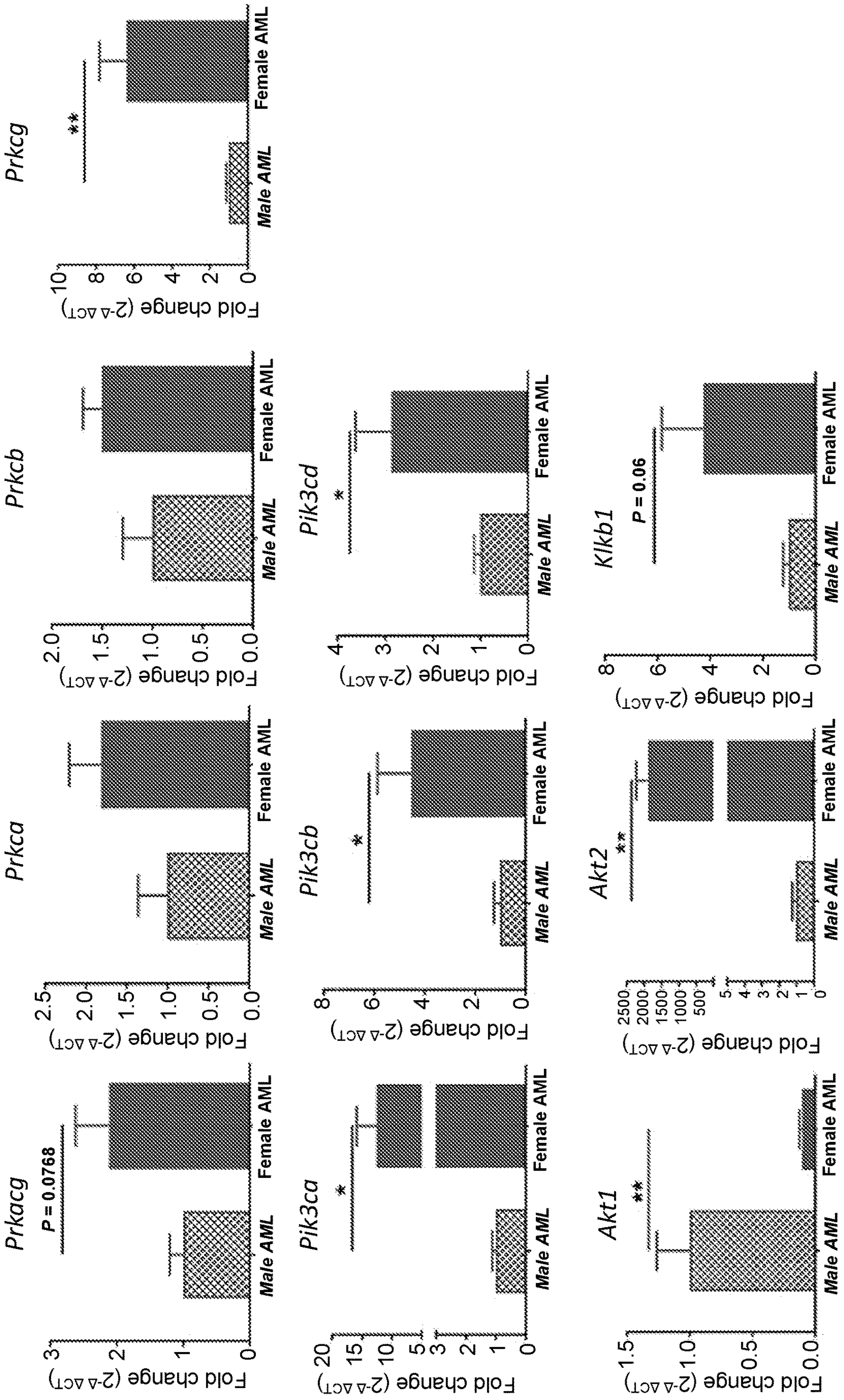

The results from this Example are shown FIGS. 3A, 3B and 3C. The results are from analysis of the expression of AR, estrogen receptors (ER), and signaling proteins for female and male AML cells.

Figure 3D:
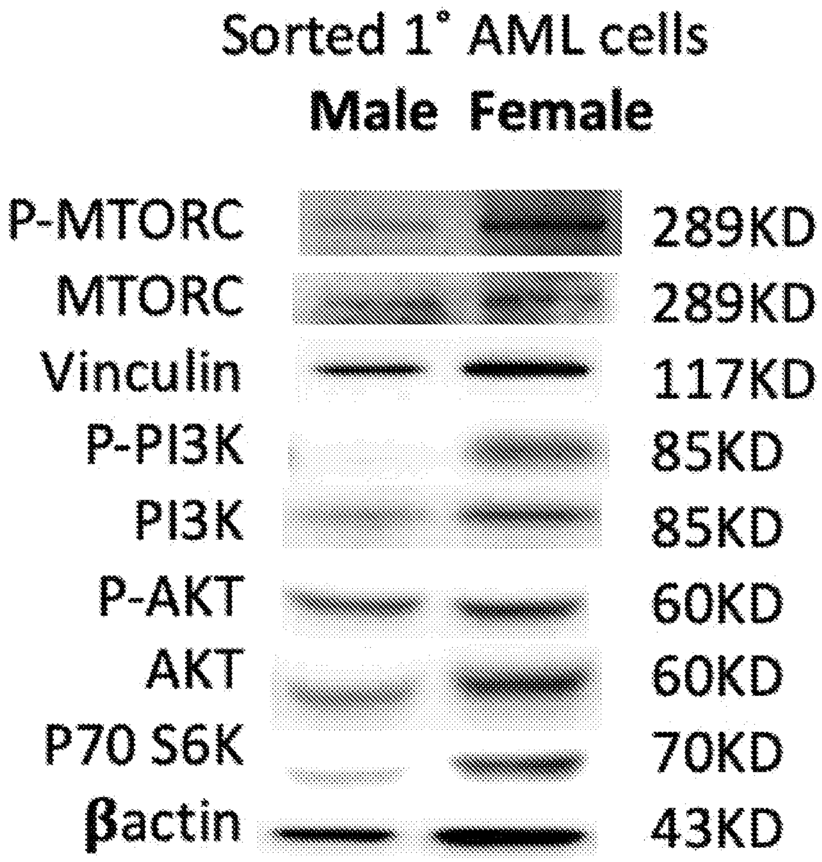

To obtain the described results, total RNA and protein were extracted from AML cells of female and male sources. (FIG. 3A) qRT-PCR results showed that expression of both androgen receptor (Ar) and estrogen receptors (Esr1 and Esr2) were increased at the mRNA level in female AML cells compared to male AML cells. (FIG. 3B) However, only AR showed significant increase in expression at the protein level in female AML cells compared to male AML cells. AR and ERα showed significant increase in expression at the protein level in female AML cells compared to male AML cells. (FIG. 3C) qRT-PCR results also showed that the expression of PI3K/AKT/MTORC signaling pathway-associated genes, including PKA (Prkacg), PKC (Prkca, Prkcb, Prkcg), PI3K (Pik3ca, Pik3cb, Pik3cd), AKT (Akt1, Akt2), and AR specific downstream target gene PSA (Klkb1) were upregulated in female AML cells comparing to male AML cells, indicating that activation of PI3K/AKT/MTORC1 signaling could be associated with AR-induced increased aggressiveness of female AML cells. (FIG. 3D) Western immunoblot results supports that the activation and expression of PI3K/AKT/MTORC signaling pathway was enhanced in female AML cells compared to male AML cells.

Because AR and PI3K/AKT/MTORC1 signaling pathway are both demonstrated to impact the outcomes in other cancers, and without intending to be constrained by any particular theory, it is considered that the increased expression of AR and PI3K/AKT/MTORC1 signaling pathway components (as well as their activities) results in increased aggressiveness of AML cells from female donors.

Example 4

Figure 4A:
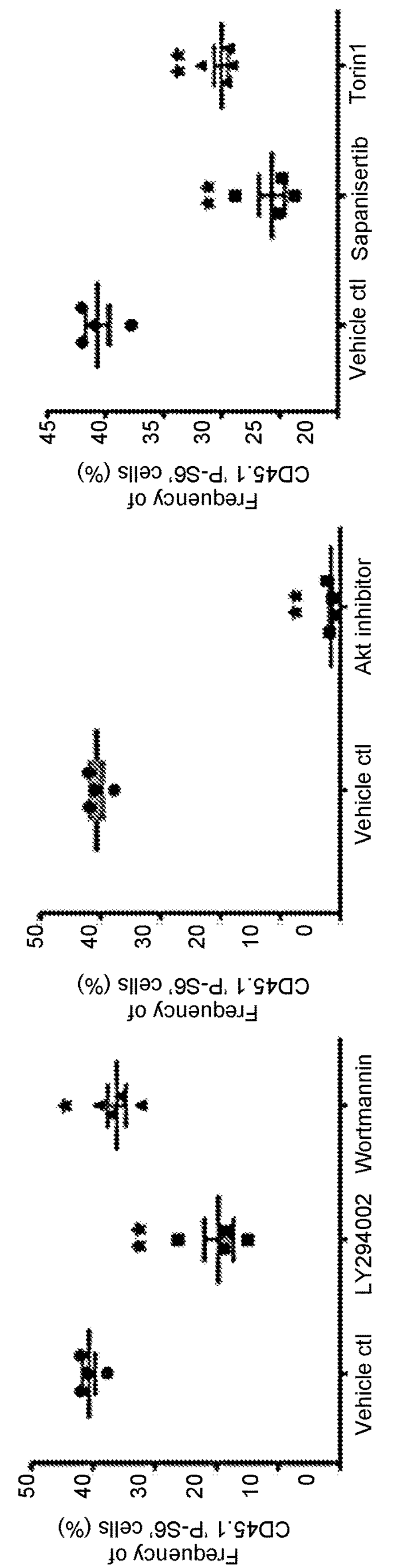
FIG. 4A, FIG. 4B, and FIG. 4C show that in vitro inhibition of PI3K/AKT/MTORC1 signaling induces apoptosis in female AML cells.
Figure 4B:
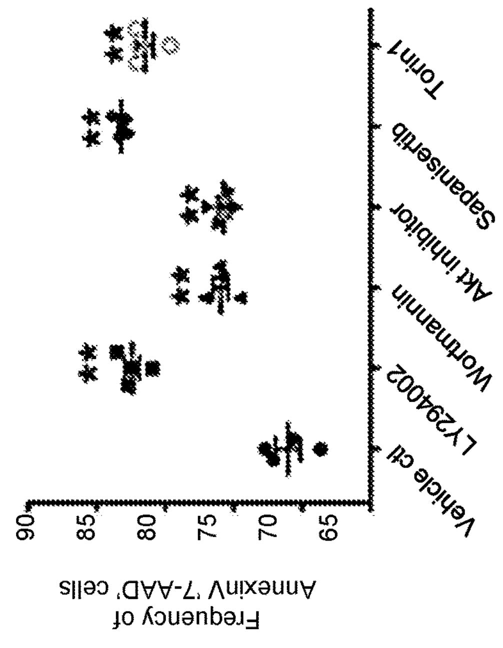
Figure 4C:
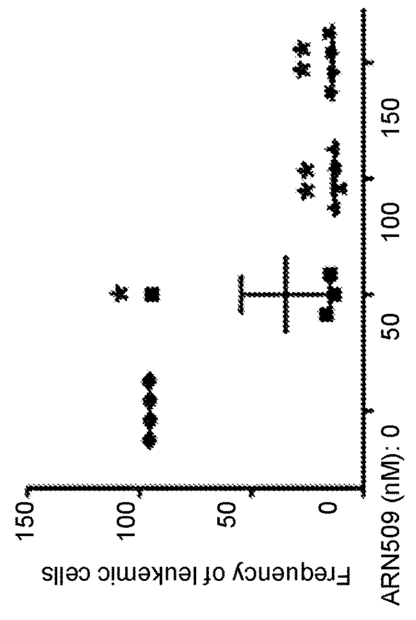

The results of this Example are shown in the indicated panels of FIG. 4 and show that in vitro inhibition of PI3K/AKT/MTORC1 signaling and AR induces apoptosis in female AML cells.

To obtain the results, isolated female AML cells were treated in vitro with PI3K inhibitors (LY294002 and Wortmannin), Akt inhibitor, MTOR inhibitors (Sapanisertib and Torin1). Phosphorylation of the downstream target P70 S6K (FIG. 4A) was down-regulated in the presence of these inhibitors. (FIG. 4B) In vitro inhibition of PI3K/AKT/MTORC signaling induced apoptosis of female AML cells significantly with Annexin V staining. (FIG. 4C) Furthermore, the application of ARN509, an antagonist of AR, also led to apoptosis of female AML cells.

These data demonstrate that AR-mediated PI3K/AKT/MTORC1 signaling pathway plays a role in the increased aggressiveness in female AML cells, and support targeting AR or PI3K/AKT/MTORC1 signaling pathway as a therapy for AML.

Example 5

The results of this Example are presented in the indicated panels of FIG. 5. The results shown in demonstrate that knockdown of AR in female AML cells decreases the aggressiveness of female AML donor cells.

Figure 5A:
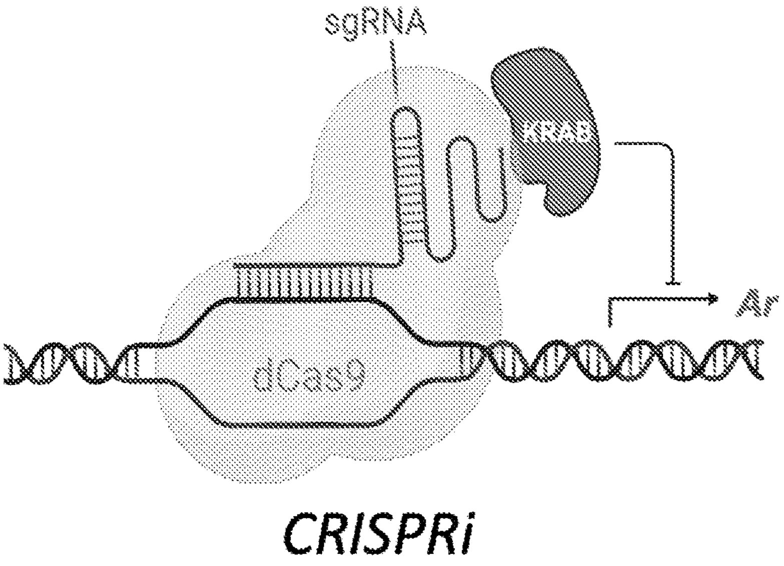
FIG. 5A, FIG. 5B, and FIG. 5C show that knockdown of AR in female AML cells decreases the aggressive of female AML donor cells.
Figure 5B:
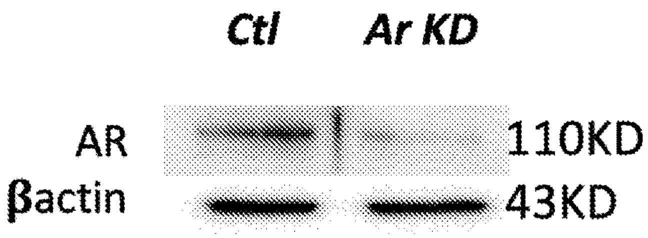

To obtain the data described in this example, we further verified the role of AR in female AML cells by genetically knocking down the expression of AR using CRISPRi technique (FIG. 5A and FIG. 5B).

Figure 5C:
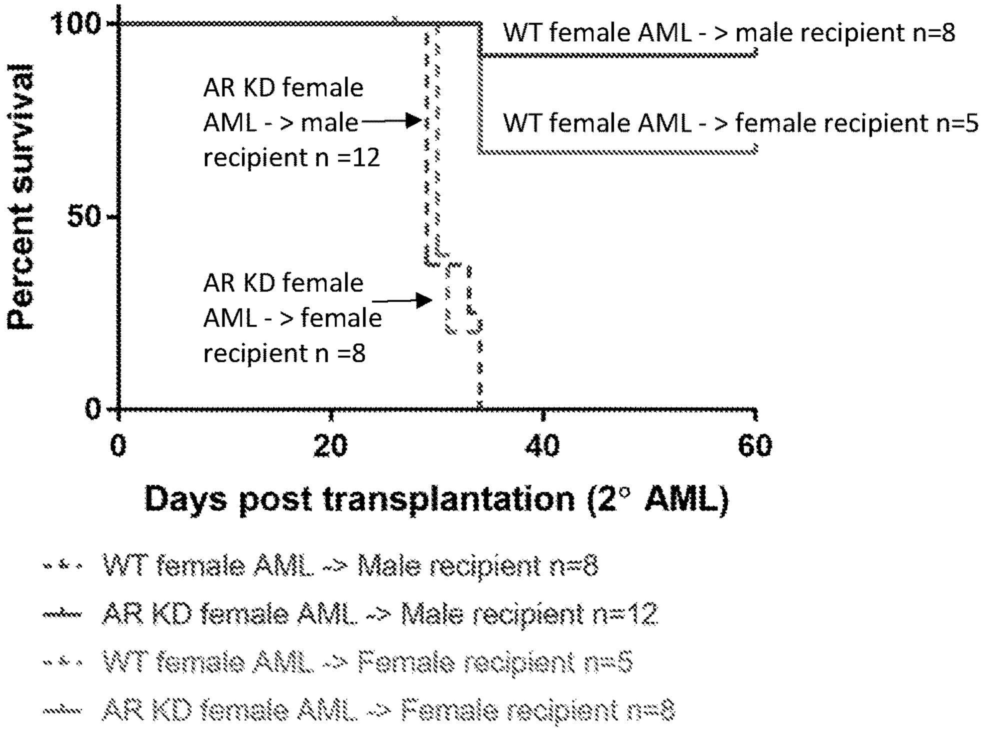

We found that decreasing the expression of AR in female AML donor cells resulted in decreased aggressiveness of these cells with respect to their ability to cause the disease in recipient mice and recipients transplanted with AR-knockdown female AML cells exhibited a significantly improvement of survival regardless of gender (FIG. 5C).

Taken together, these data demonstrate that increased AR expression resulted in the increased aggressiveness of female AML cells.

Example 6

The results of this Example are presented in the indicated panels of FIG. 6, and show that KO of RAPTOR in female AML cells decreases the aggressive of female AML donor cells.

As described above, an enhanced PI3K/AKT/MTORC signaling pathway leads to the increased aggressiveness of female AML cells. Therefore, we sought to manipulate this pathway by genetically deleting a component of MTORC1, RAPTOR, in female AML cells.

Figure 6A:
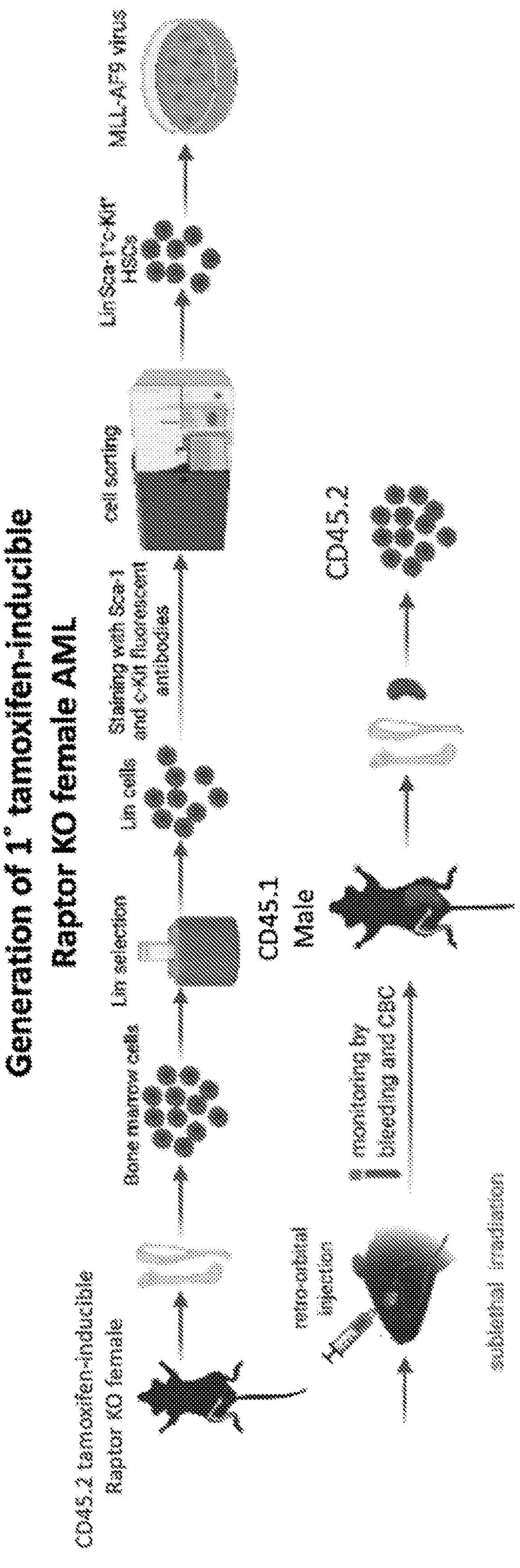
FIG. 6A, FIG. 6B, FIG. 6C, FIG. 6D, FIG. 6E, and FIG. 6F show that Knockout (KO) of RAPTOR in female AML cells decreases the aggressive of female AML donor cells.
Figure 6B:
Figure 6C:
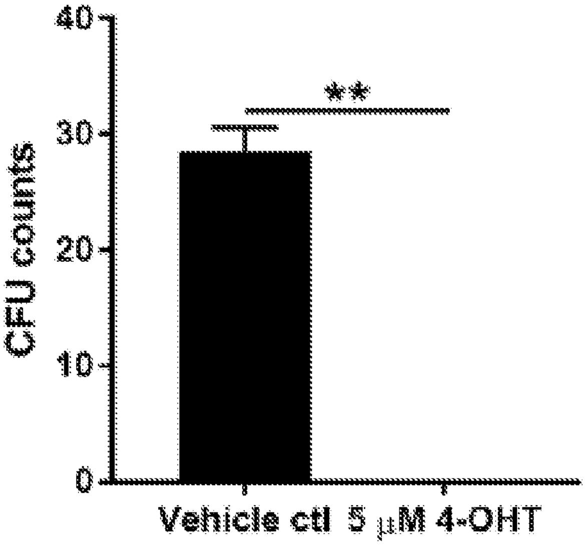
Figure 6D:
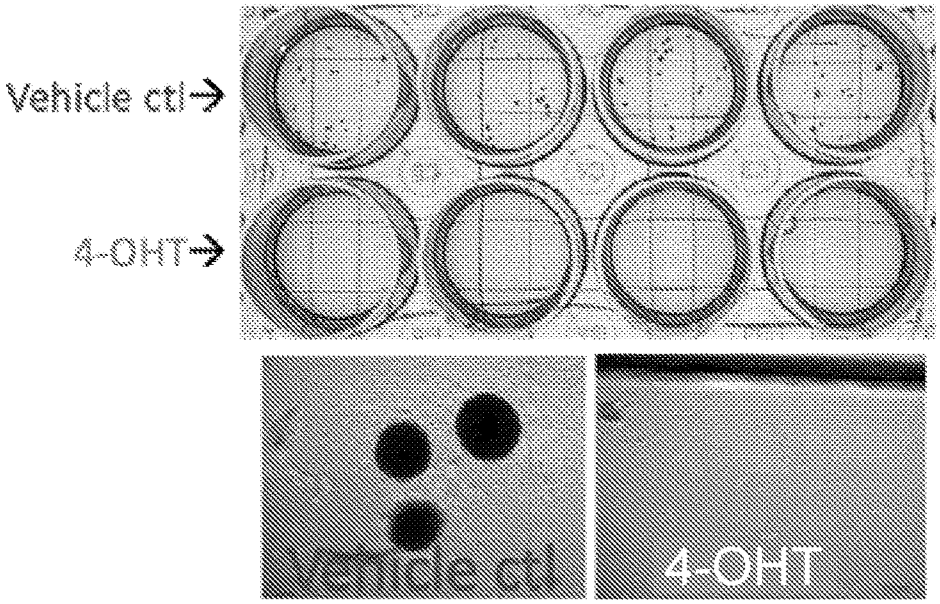
Figure 6E:
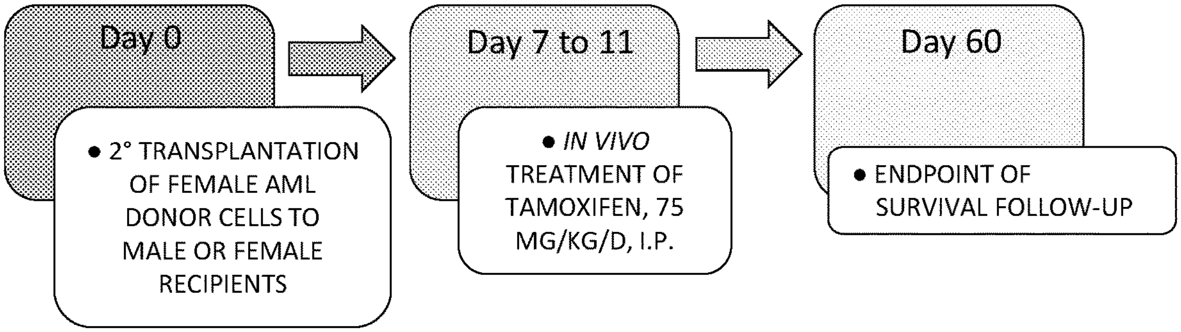
Figure 6F:
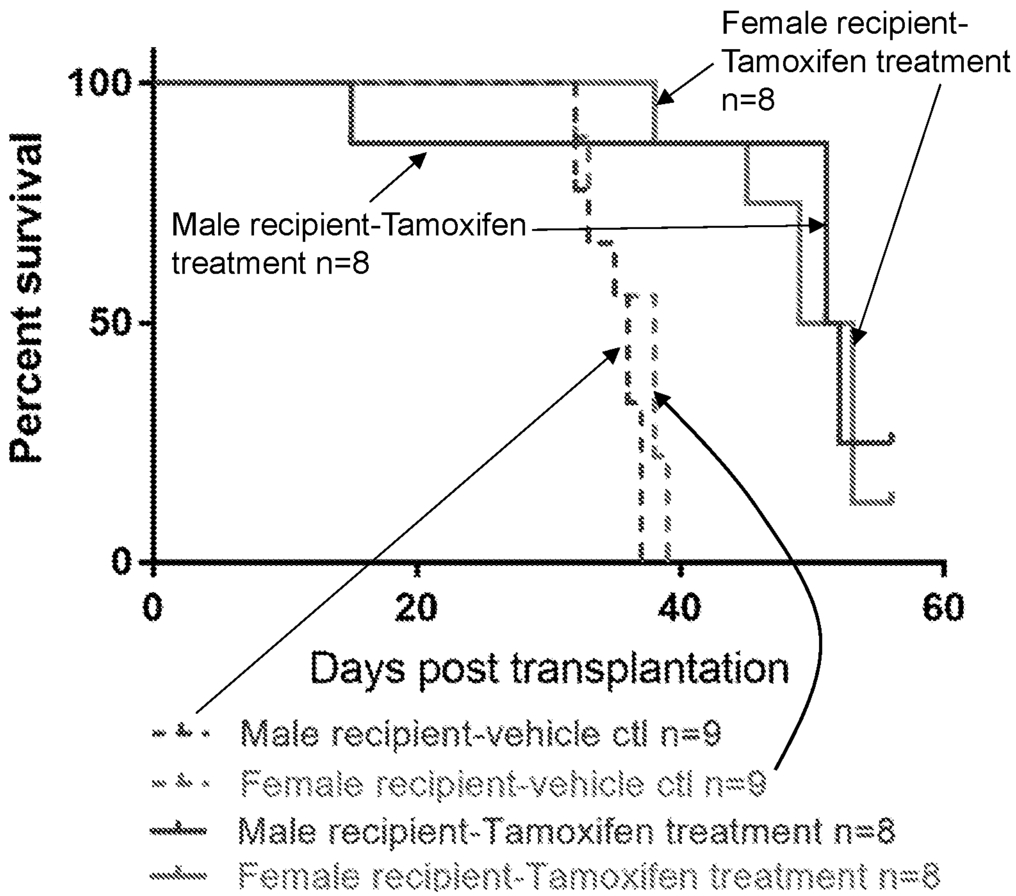
Figure 7A:
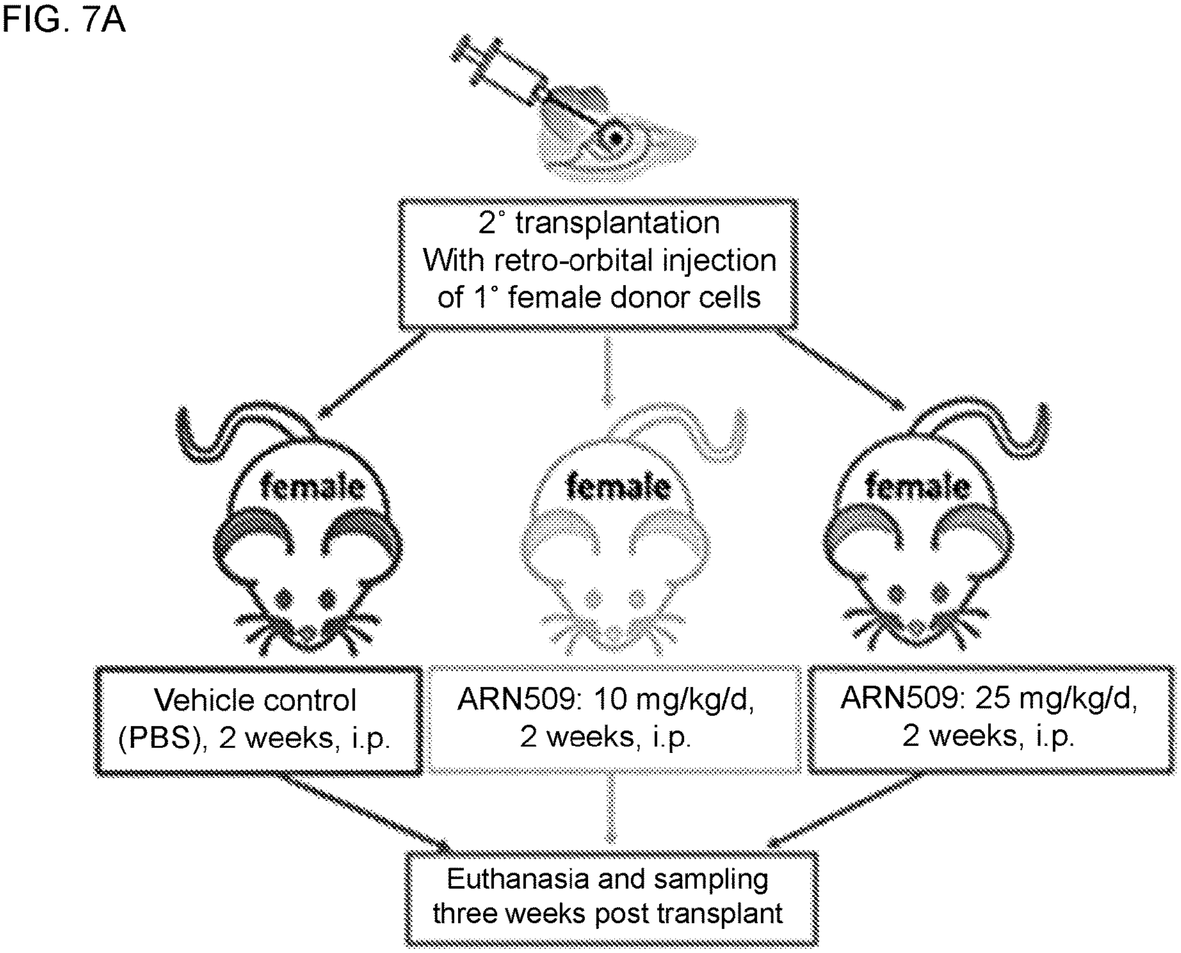
FIG. 7A, FIG. 7B, FIG. 7C, FIG. 7D, FIG. 7E, FIG. 7F, FIG. 7G, FIG. 7H, FIG. 7I, and FIG. 7J show in vivo treatment of ARN509 decreases the severity of AML in female mice transplanted with female AML donor cells.
Figure 7B:
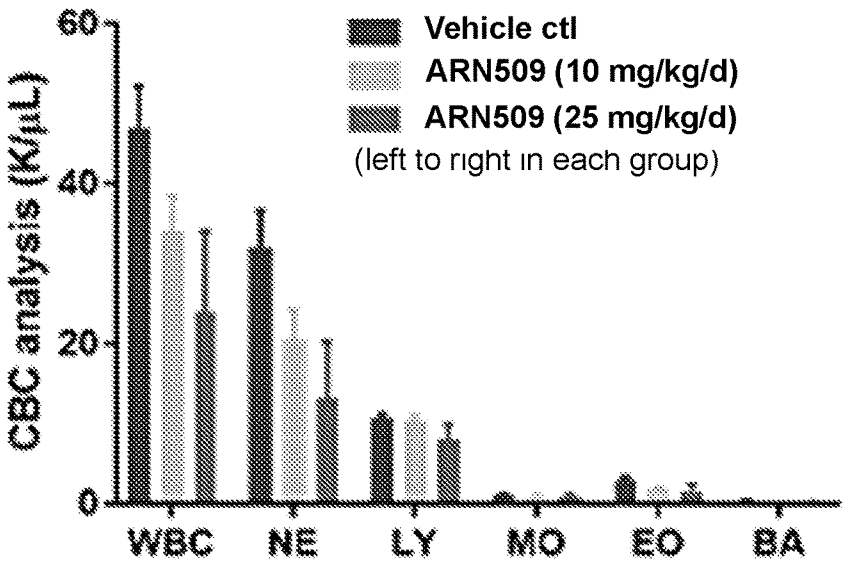
Figure 7C:
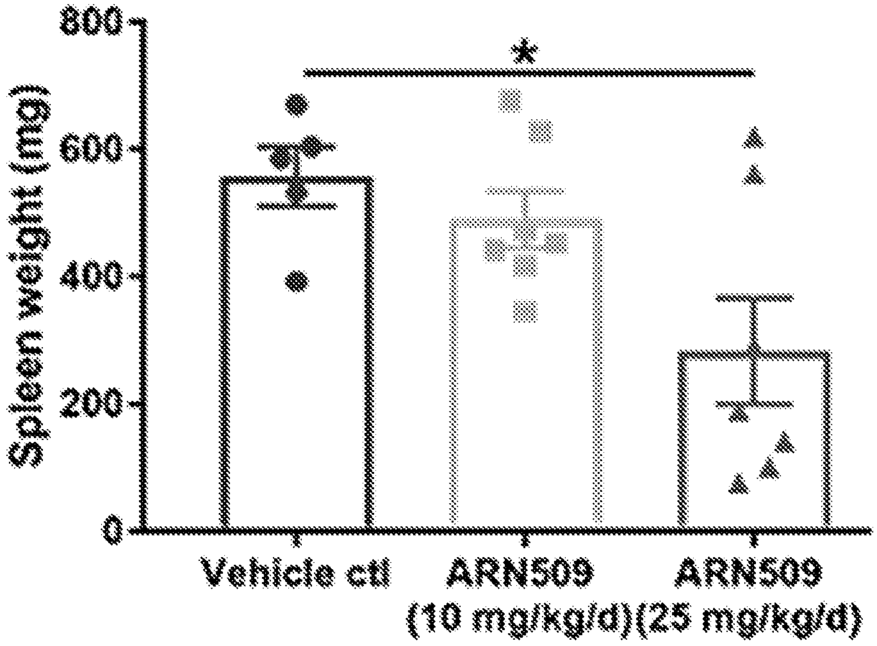
Figure 7D:
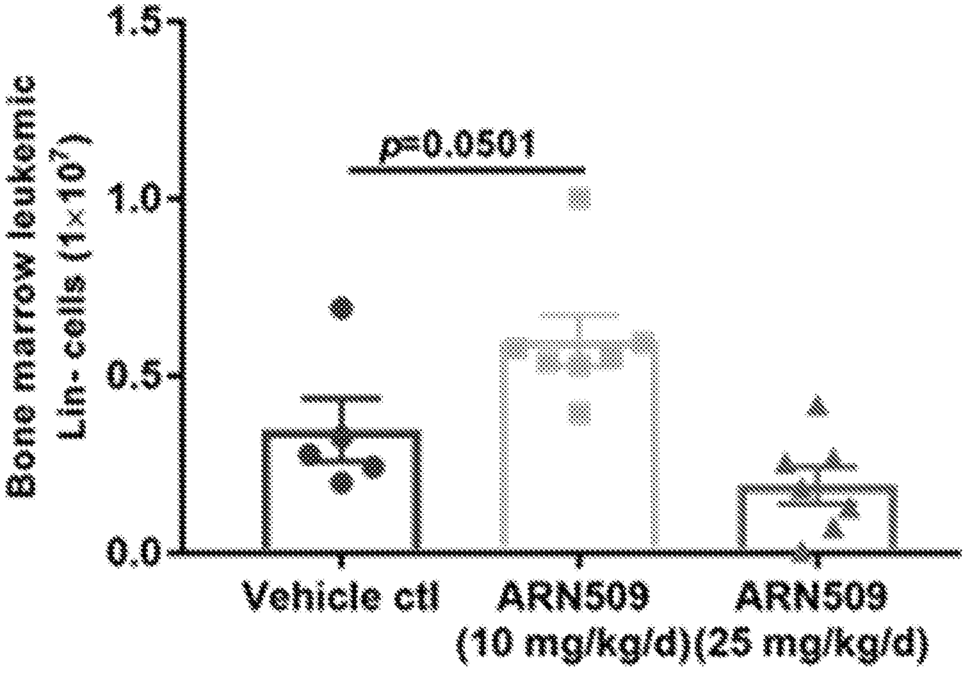
Figure 7E:
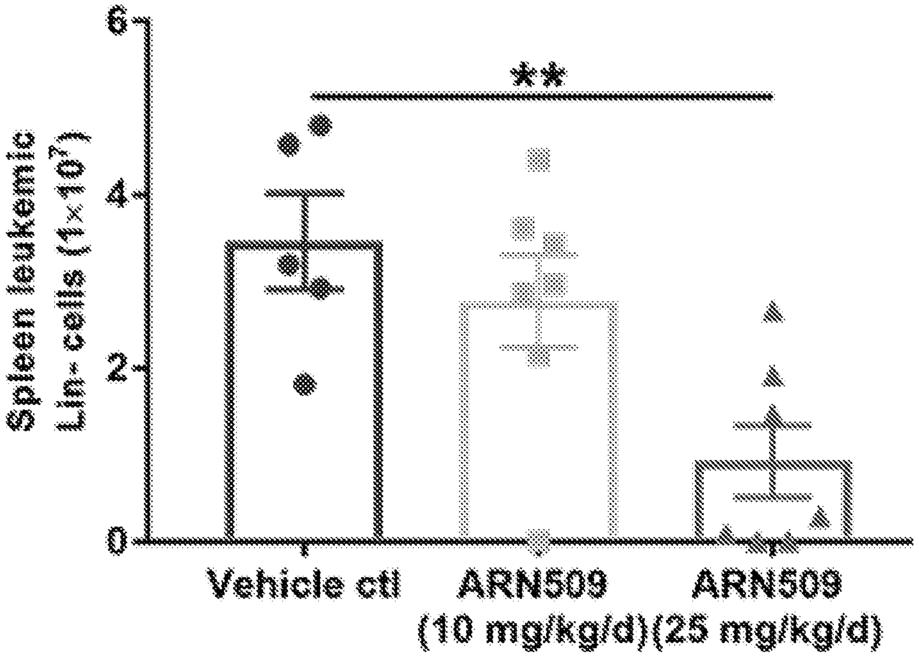
Figure 7F:
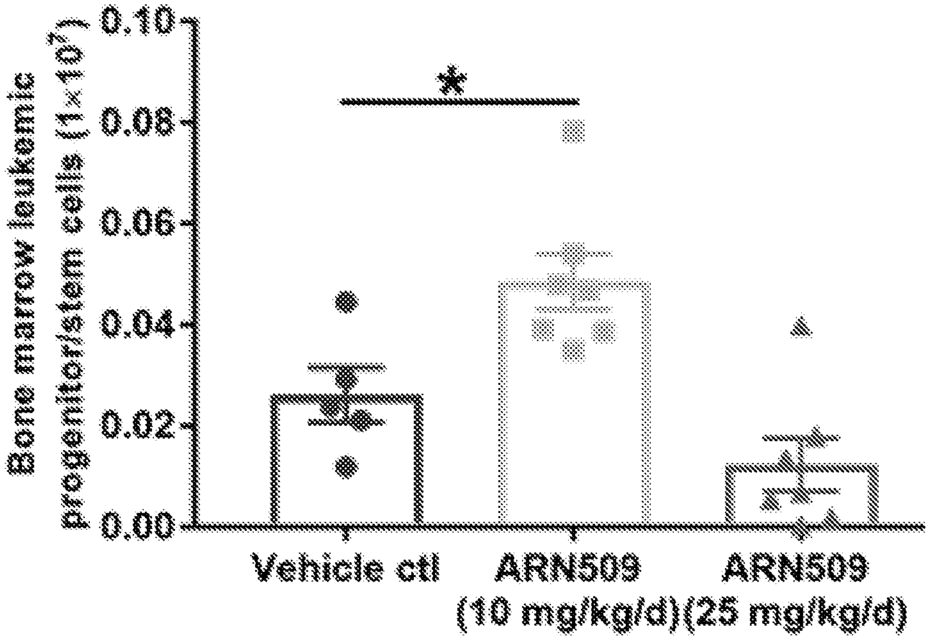
Figure 7G:
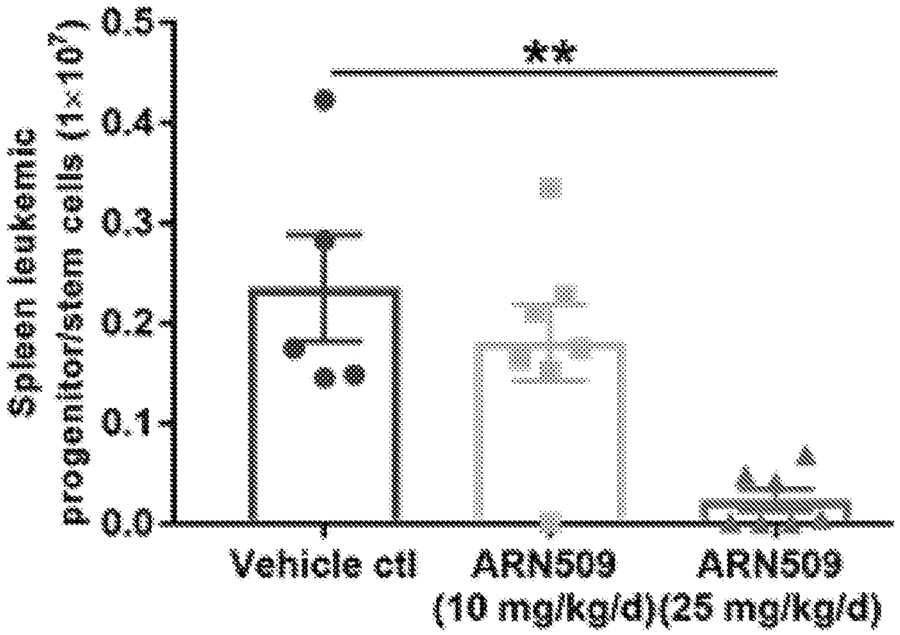
Figure 7H:
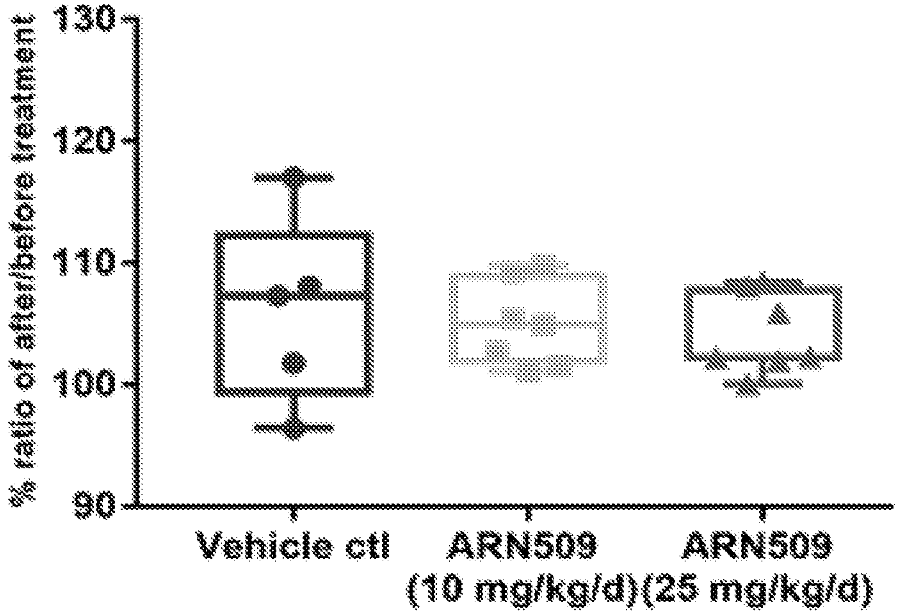
Figure 7I:
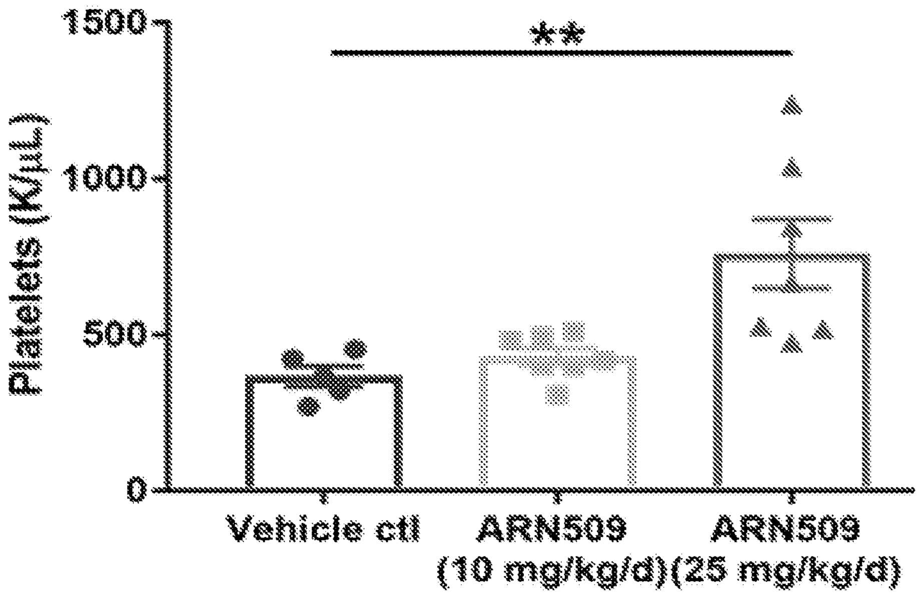
Figure 7J:
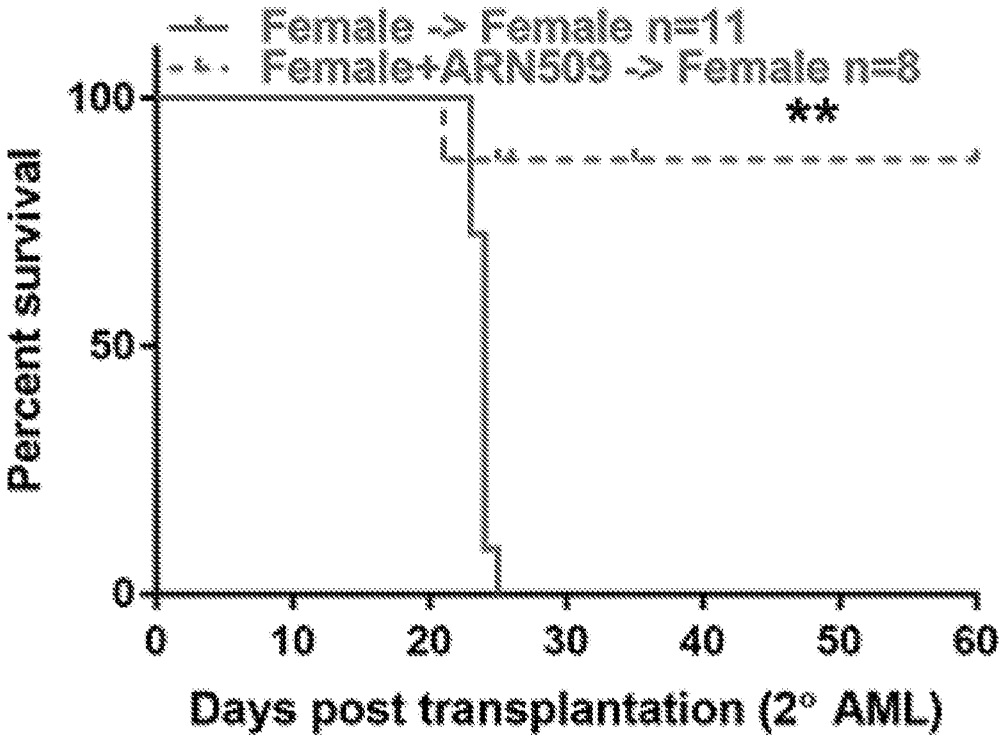

We used CD45.2 tamoxifen-inducible Raptor KO female mice, and isolated HSCs from them (FIG. 6A). AML cells were generated as in FIG. 1. The KO of RAPTOR was confirmed by treating the AML cells in vitro with 5 μM 4-hydroxytamoxifen (4-OHT) for 24 h followed by western blotting. The expression of RAPTOR in female AML cells was markedly decreased upon 4-OHT induction (FIG. 6B). RAPTOR KO in female AML cells resulted in the inability of colony formation of female AML cells (FIG. 6C and FIG. 6D). Furthermore, transplantation of the tamoxifen-inducible Raptor KO female AML cells into either female or male recipients followed by treatment with tamoxifen (75 mg/kg/d, i.p.) for five days to induce the KO of RAPTOR in AML cells (FIG. 6E) indicated that recipients (both male and female) had improved survival upon treatment with tamoxifen.

Taken together, these data further confirm that the enhanced PI3K/AKT/MTORC1 signaling pathway leads to the increased aggressiveness of female AML cells.

Example 7

The results of this Example are presented in the indicated panels of FIG. 7 which show that in vivo treatment of ARN509 decreases the severity of AML in female mice transplanted with female AML donor cells.

To test the effect of AR inhibition on the outcome of AML, we utilized the AR antagonist, ARN509, to treat female mice transplanted with female AML donor cells. (FIG. 7A) Following one week post-secondary (2°) transplantation of AML cells from female donors into female recipients, the recipient mice were treated with ARN509 (0, 10, 25 mg/kg/d, i.p. injection) daily for two weeks. In vivo antagonism of AR decreased the severity of AML in a dose-dependent manner featured by improved leukocytosis (FIG. 7B) and splenomegaly (FIG. 7C) in AML female recipients. Additionally, $Lin^-$ leukemic cells in the bone marrow (FIG. 7D) and spleen (FIG. 7E) were decreased significantly by 25 mg/kg/d ARN509, as well as LICs (FIG. 7F and FIG. 7G), a population which underlies the relapse of AML. On the other hand, in vivo treatment of ARN509 showed no apparent side effects with unchanged body weight (FIG. 7H), but with an increase in platelets in the peripheral blood. (FIG. 7J) Moreover, female recipients transplanted with female AML donors which were treated by in vitro ARN509 (150 nM, 24 h) also had significantly better survival than their counterparts.

These data demonstrate that antagonism of AR benefits the survival of female AML by eliminating LICs without apparent side effects, supporting the use of ARN509 as a therapy in AML patients.

Example 8

The results of this Example are presented in the indicated panels of FIG. 8, which show that in vivo treatment of ARN509 decreases the severity of AML in male mice transplanted with female AML donor cells.

To address if ARN509 therapy preferentially benefitted AML in female mice, we performed an experiment in which male recipient mice transplanted with female AML donors cells were treated with AR antagonist, ARN509. This approach shows that regardless of the gender of the recipient, antagonism of AR in female AML cells can alleviate the severity of disease.

Figure 8A:
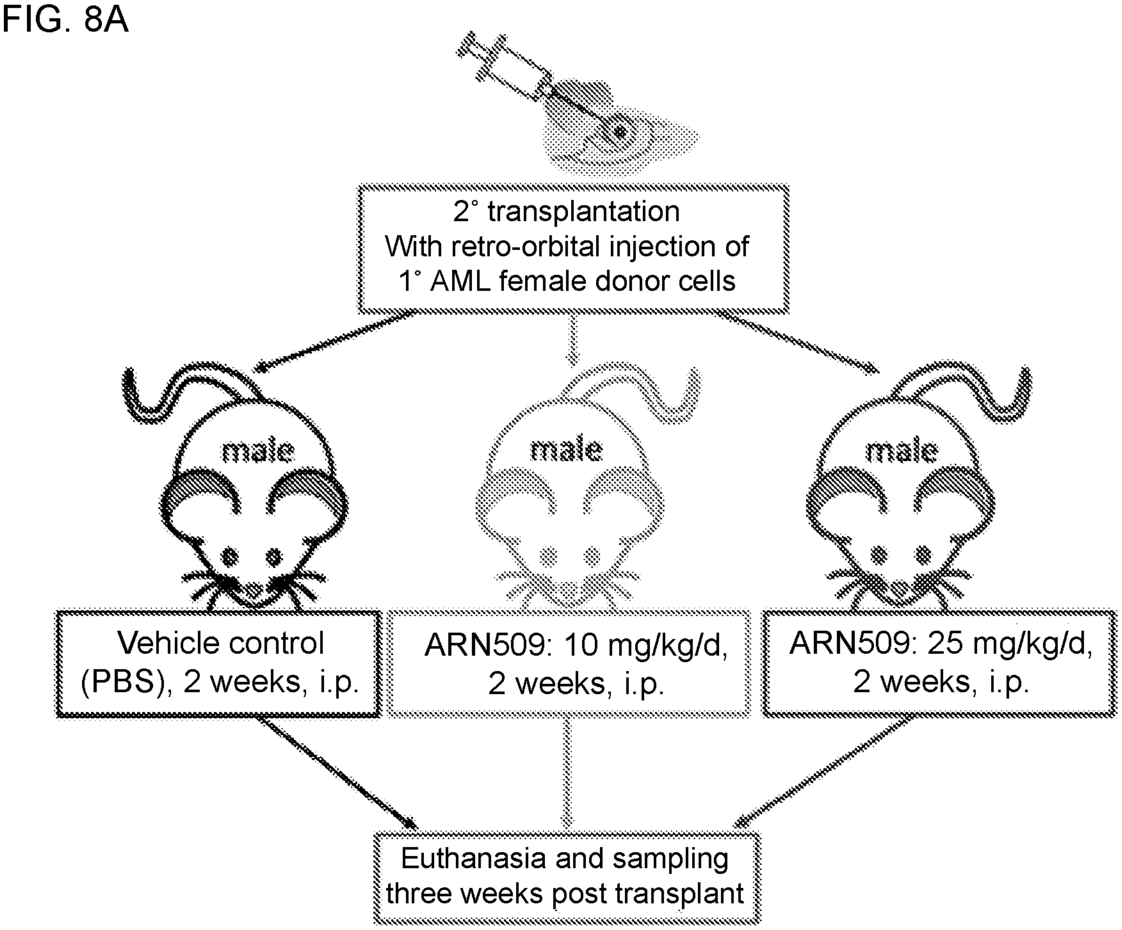
FIG. 8A, FIG. 8B, FIG. 8C, FIG. 8D, FIG. 8E, FIG. 8F, FIG. 8G, FIG. 8H, FIG. 8I, and FIG. 8J show that in vivo treatment of ARN509 decreases the severity of AML in male mice transplanted with female AML donor cells.
Figure 8B:
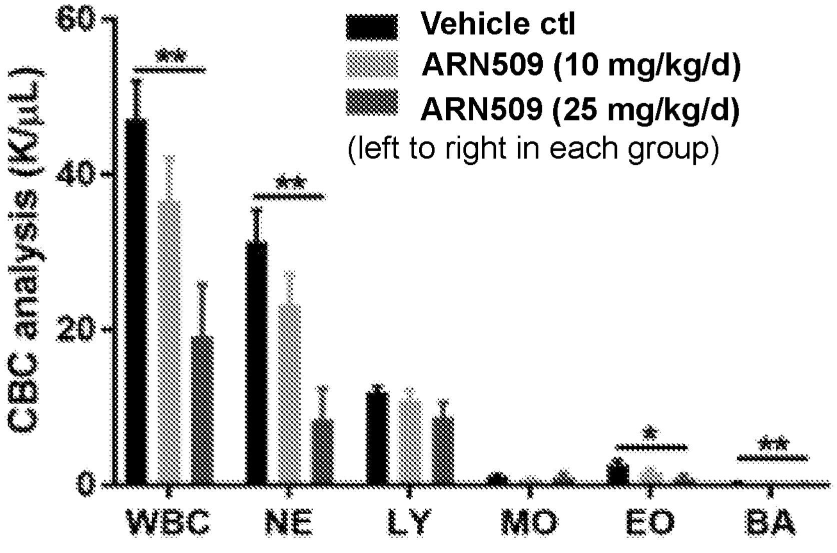
Figure 8C:
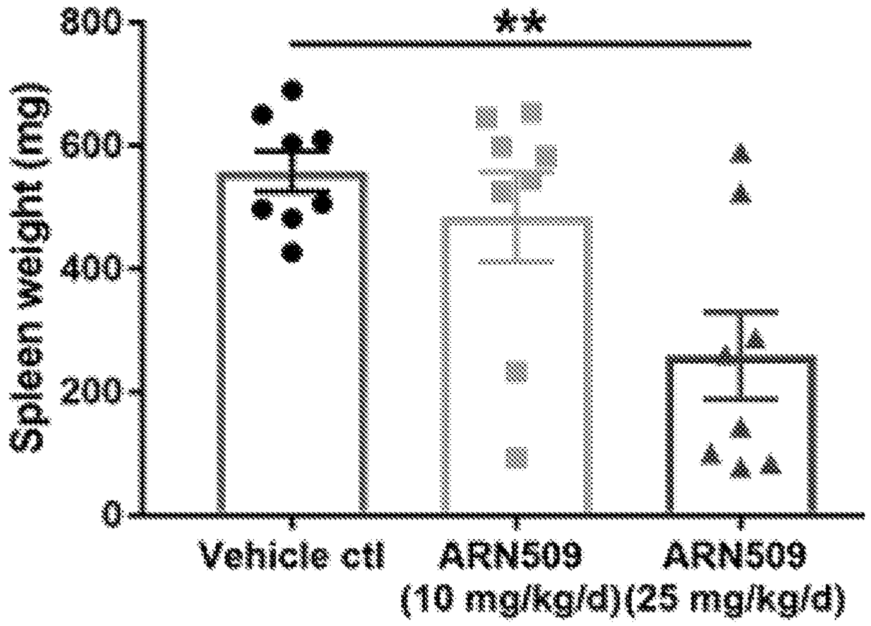
Figure 8D:
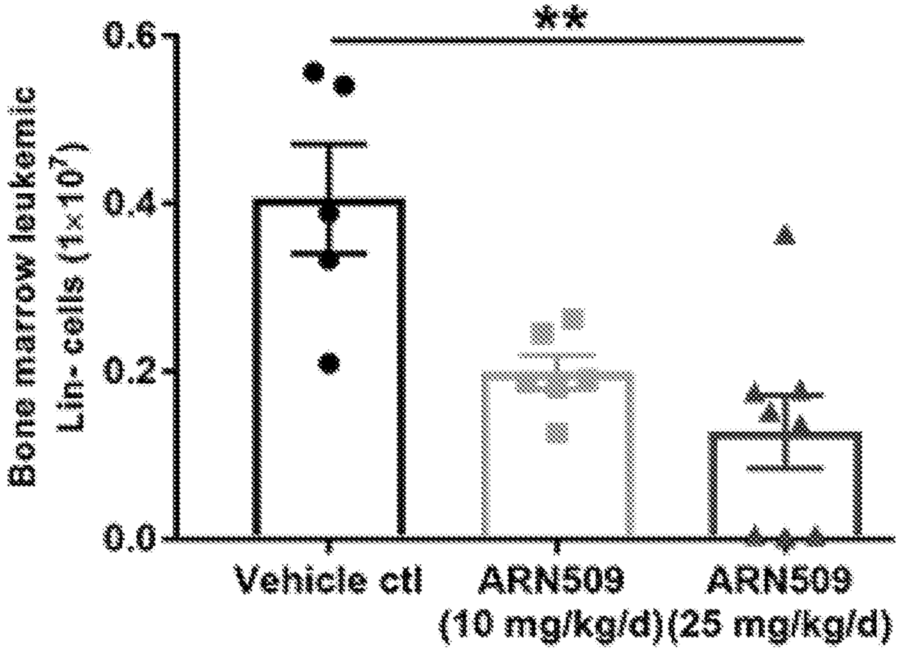
Figure 8E:
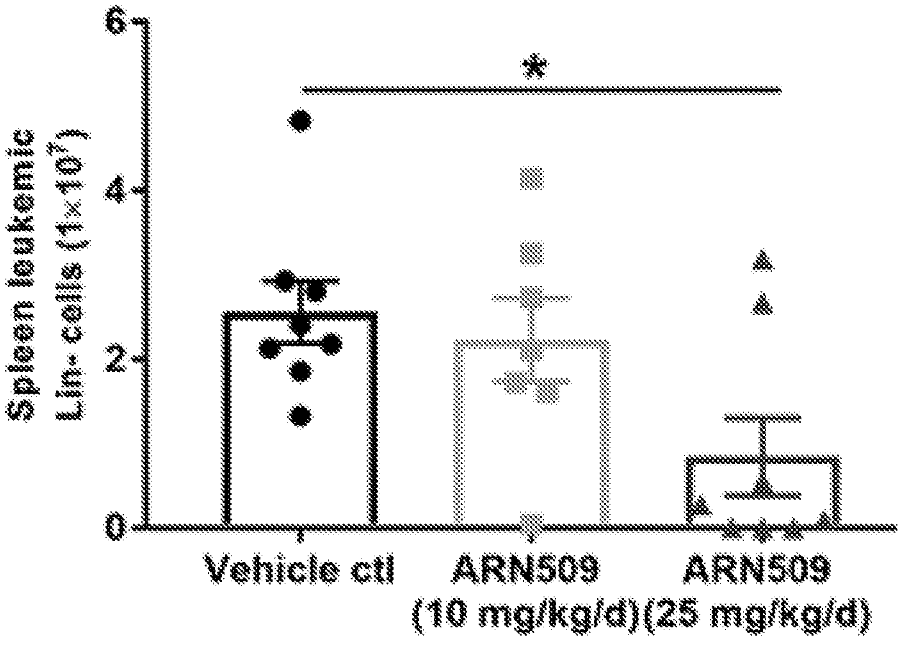
Figure 8F:
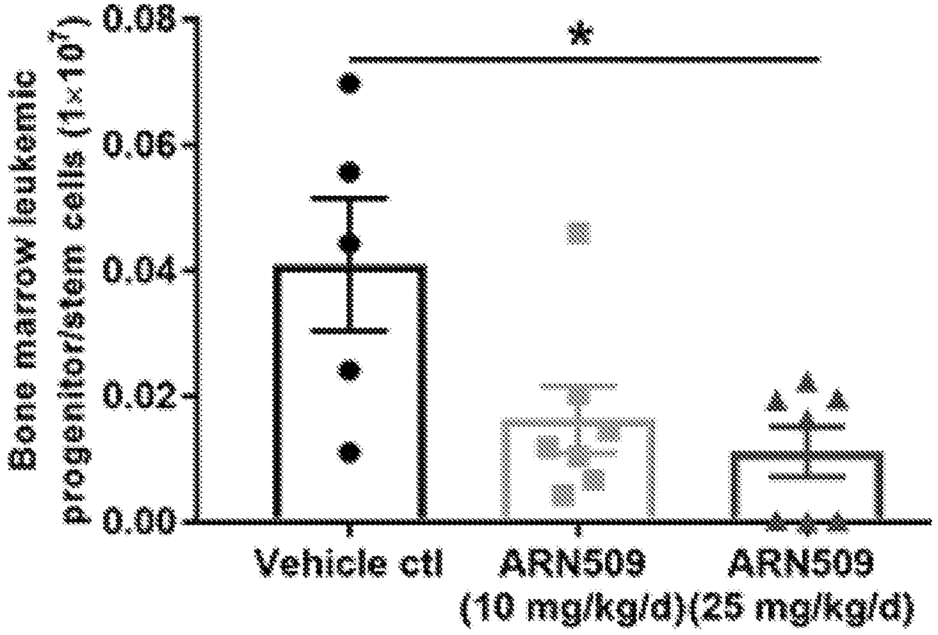
Figure 8G:
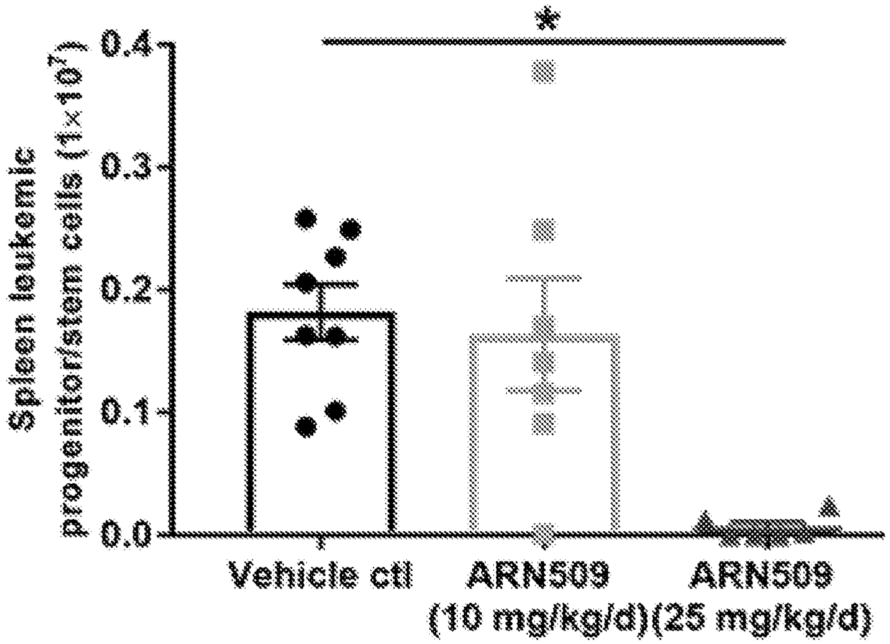
Figure 8H:
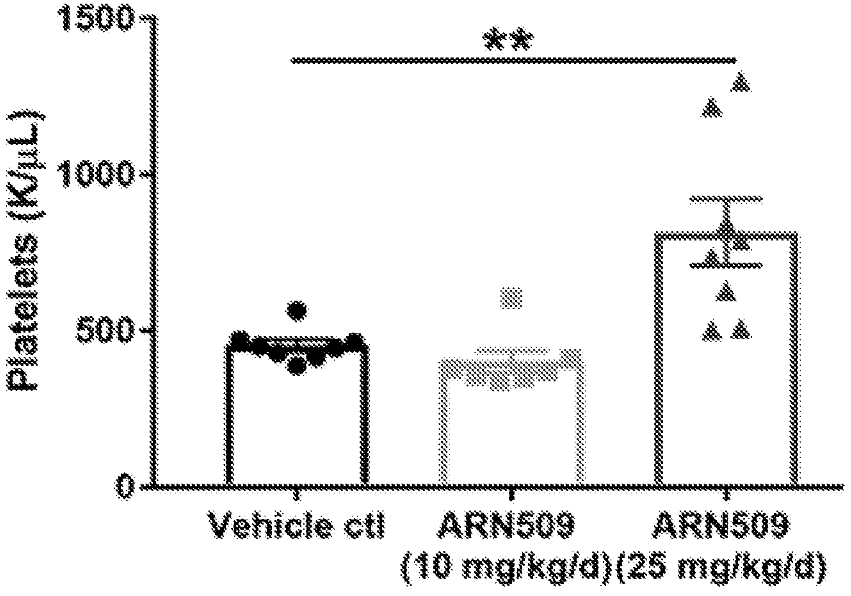
Figure 8I:
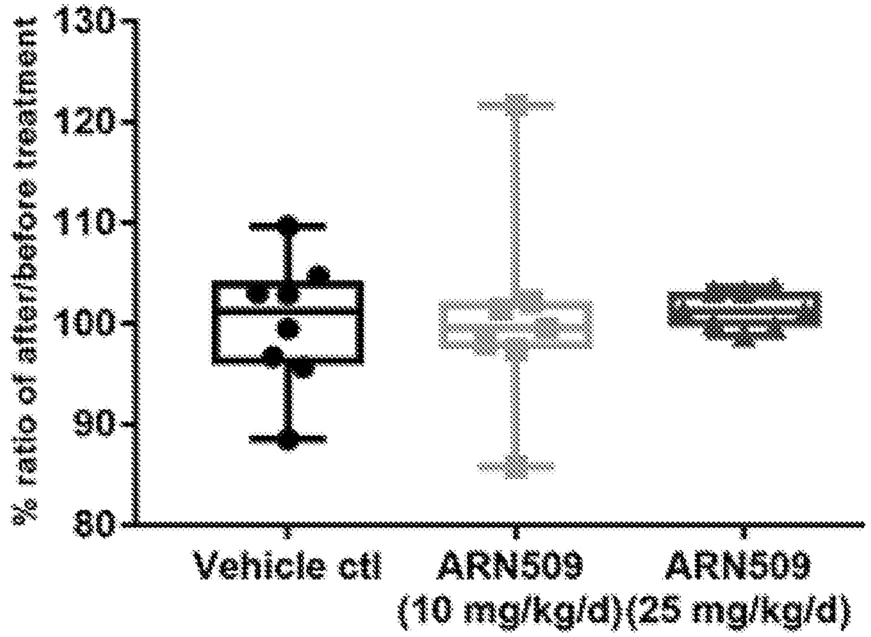
Figure 8J:
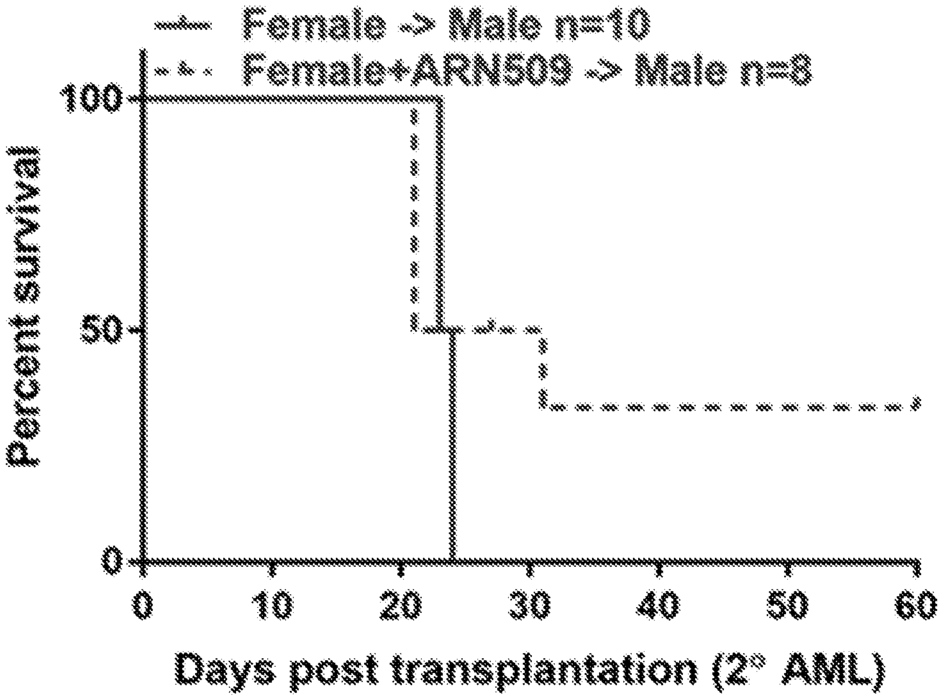

(FIG. 8A) Following one week post 2° transplantation of AML cells from female donors into male recipients, we treated the mice with ARN509 (0, 10, 25 mg/kg/d, i.p. injection) for two weeks. We found that in vivo antagonism of AR decreased the severity of AML in a dose-dependent manner featured by improved leukocytosis (FIG. 8B) and splenomegaly (FIG. 8C) in AML male recipients. Specifically, $Lin^-$ leukemic cells in the bone marrow (FIG. 8D) and spleen (FIG. 8E) were decreased significantly by 25 mg/kg/d ARN509, as well as LICs (FIG. 8F and FIG. 8G). On the other hand, in vivo treatment of ARN509 also showed no apparent side effects, but still showed an increase in platelets in the peripheral blood (FIG. 8H) and unchanged body weight (FIG. 8I). Unexpectedly, male recipients transplanted with female AML donors, which were treated by in vitro ARN509 (150 nM, 24 h) showed some improvement of survival compared to their counterparts; but not as significant as female recipients transplanted with ARN509-treated female AML donors (FIG. 8J).

These data further demonstrate the effect of ARN509 on female AML cells in the background of male recipients. The modest improvement of survival (FIG. 8J) indicates that male recipients lack the protective mechanism as in female recipients (also corroborated in FIG. 1D).

Example 9

The results of this Example are presented in the indicated panels of FIG. 9, which shows that ovariectomy of female recipient mice fails to change the outcome of AML.

To explore the protective mechanism of female recipients, we analyzed whether female recipients exhibited: 1) more estrogen generation, or 2) less androgen generation than male recipients. To rule out the first possibility, AML donor cells (of mixed gender) were transplanted into ovariectomized (OVX) female recipients and OVX-sham control recipients.

Even though we observed a modest increased white blood cell (WBC) level in the peripheral blood of OVX-mice post transplantation (FIG. 9A), we failed to see any difference in the survival (FIG. 9B). When analyzed the outcome of the mice (FIG. 9C), we found OVX-mice exhibited better prognosis than the control mice. These data suggest that higher estrogen levels in female mice may not be the protective mechanism helping them combat cancer cells.

We also tested a second possibility that less androgen generation may be a protective mechanism in the female mice. The results indicate that higher androgen level in male mice may be an unfavorable factor, facilitating the expansion of AML donor cells during transplantation.

Example 10

The results of this Example are presented in indicated panels of FIG. 10, and show a survival analyses of the effect of active androgen production in male mice transplanted with male AML donor cells.

As DHT is the most active form of testosterone metabolite that is known for ligand-dependent activation of AR, we utilized finasteride, a 5-α reductase inhibitor, to reduce the formation of DHT in male recipient mice transplanted with male AML donor cells. Through this approach, we demonstrate that decreased endogenous DHT generation could serve as a protective mechanism in female recipients.

Figure 10A:
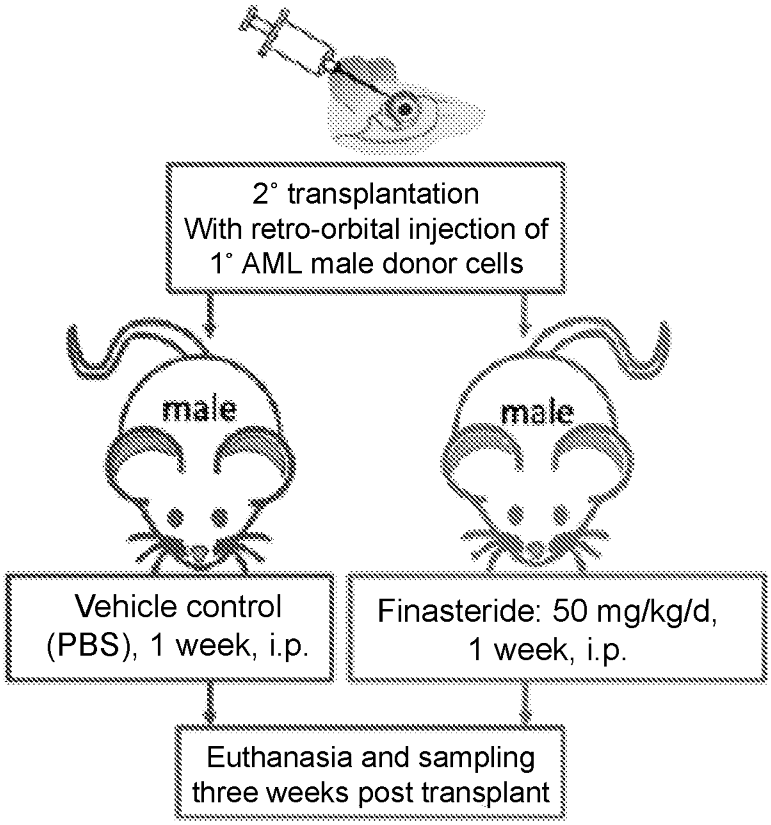
FIG. 10A, FIG. 10B, FIG. 10C, FIG. 10D, FIG. 10E, FIG. 10F, FIG. 10G, FIG. 10H, FIG. 10I, and FIG. 10J show mechanistic and survival analyses of the effect of active androgen production in male mice transplanted with male AML donor cells.
Figure 10B:
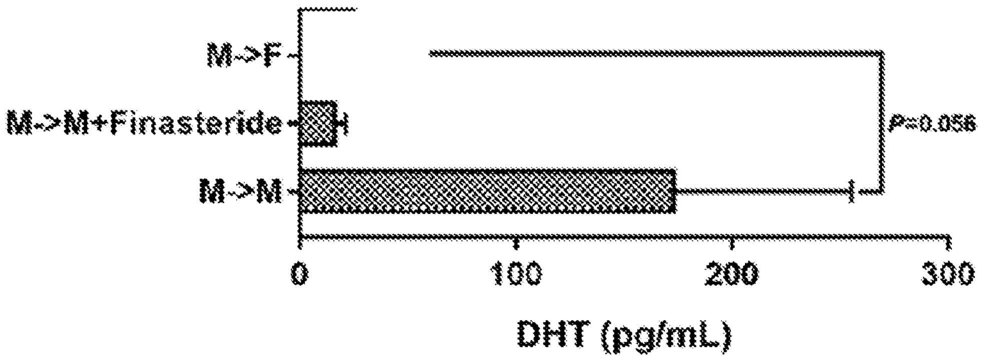
Figure 10C:
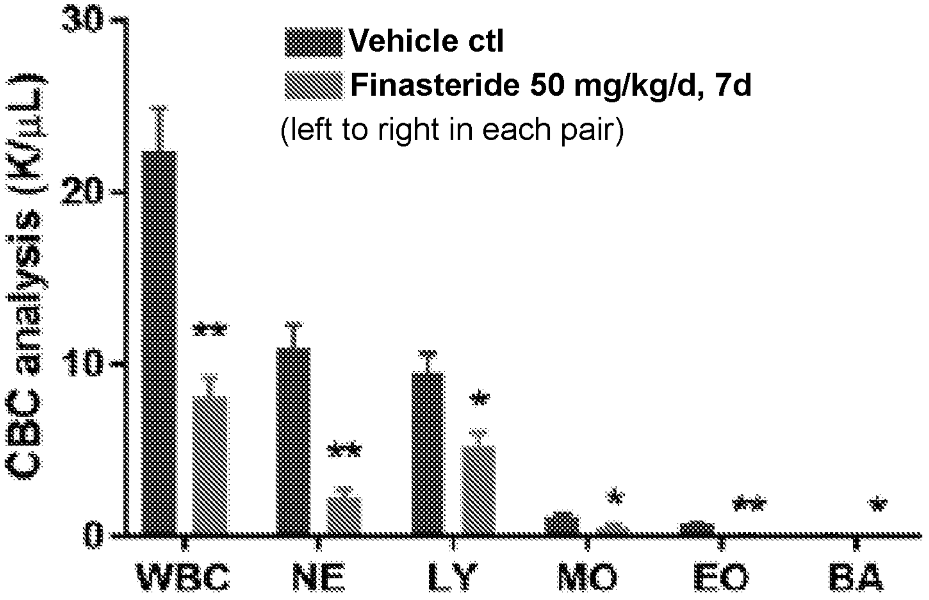
Figure 10D:
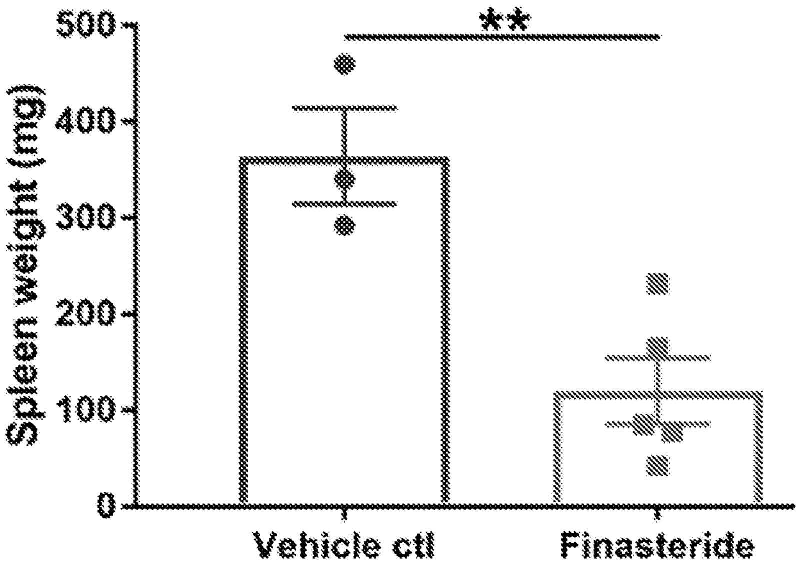
Figure 10E:
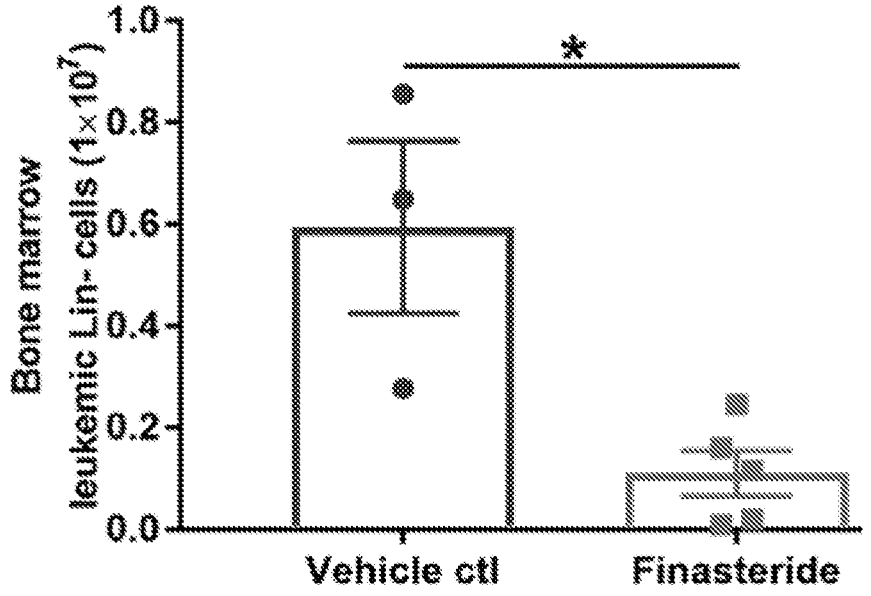
Figure 10F:
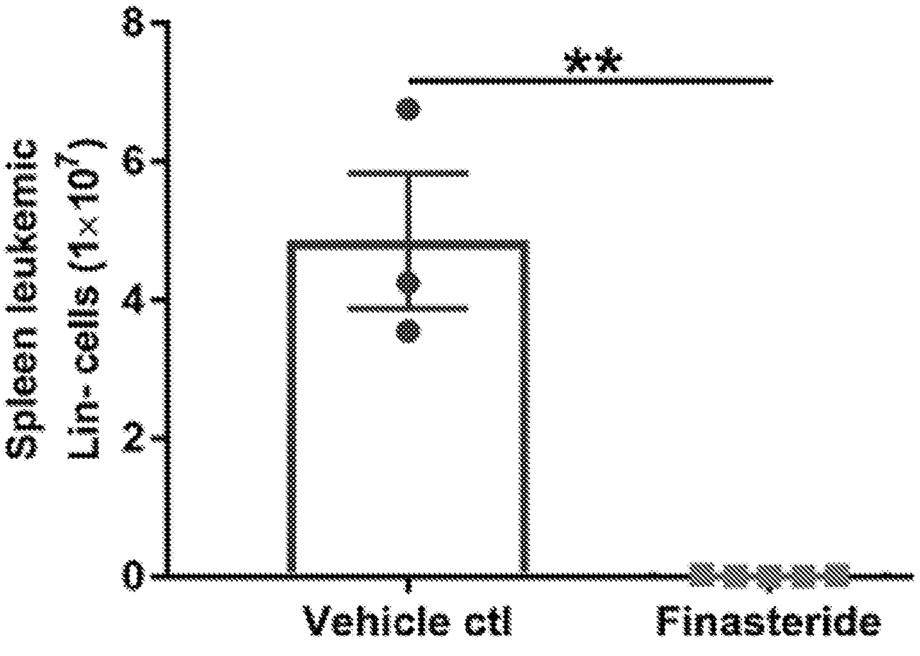
Figure 10G:
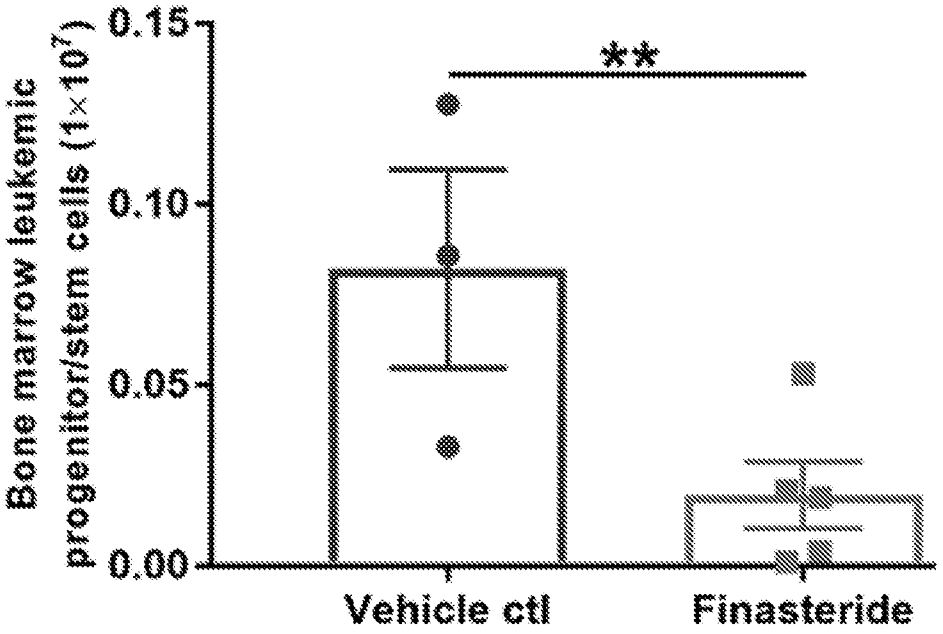
Figure 10H:
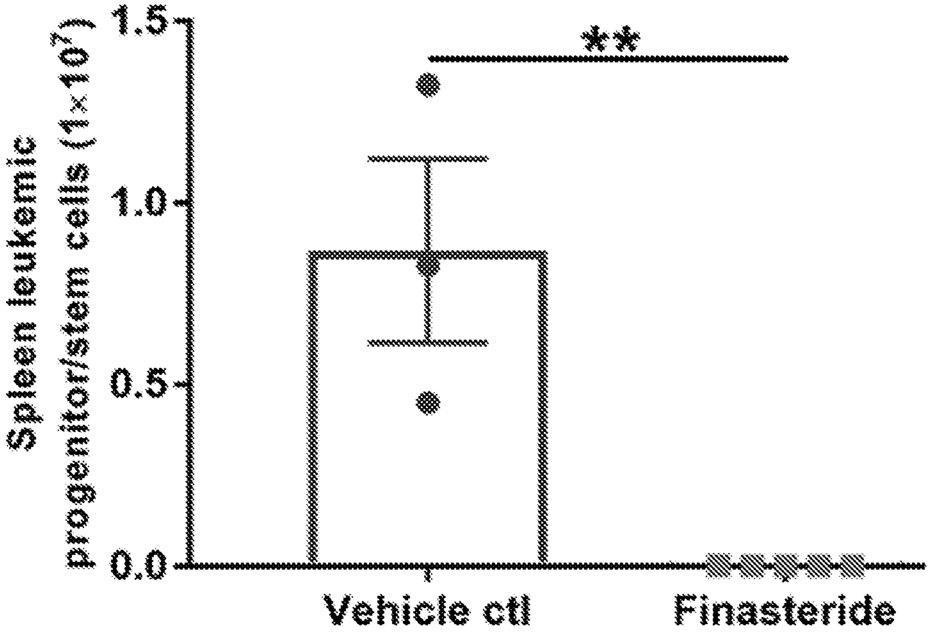
Figure 10I:
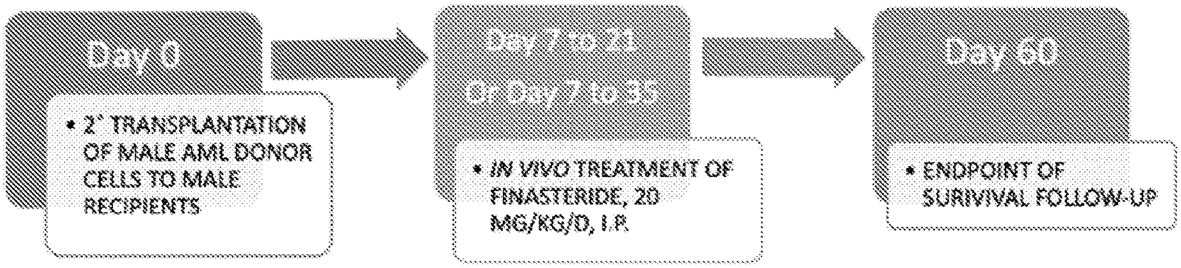
Figure 10J:
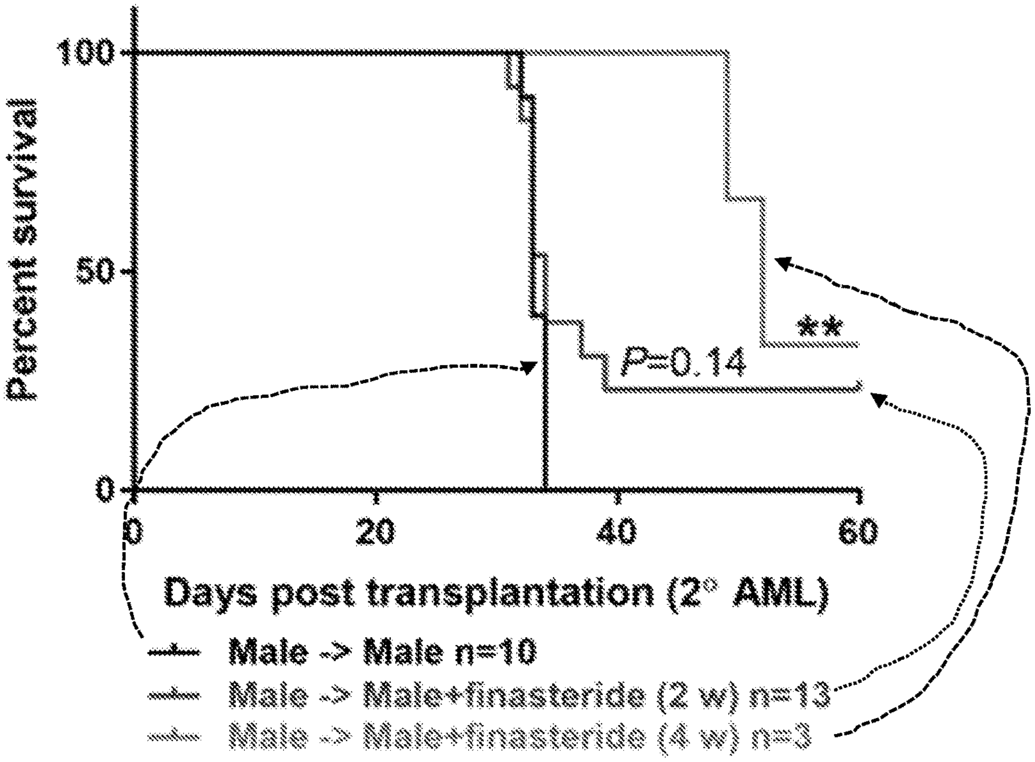

(FIG. 10A) Upon 2° transplantation of male AML donors to male recipients, the recipient mice were treated with vehicle (PBS) or finasteride (50 mg/kg/d, i.p. injection) for one week. Then at three weeks post transplantation, mice were euthanized. As shown in the figure, inhibition of 5-α reductase by finasteride led to a decreased generation of DHT (FIG. 10B) and significantly improved leukocytosis (FIG. 10C) and splenomegaly (FIG. 10D). Finasteride significantly reduced the leukemic burden in the bone marrow and spleen shown as decreased $Lin^-$ leukemic cells (FIG. 10E and FIG. 10G) and LICs (FIG. 10F and FIG. 10H). Moreover, to observe the therapeutic effect of finasteride, we treated male recipients transplanted with male AML donors (mirroring the clinical patients) with in vivo finasteride for two weeks or extended it to four weeks (FIG. 10I). A two-week finasteride treatment partially benefited the survival of male recipients transplanted with male AML donors without achieving statistical significance, while four-week treatment significantly improved the survival (FIG. 10J). Thus, the disclosure includes adjusting the treatment period for male (and female) AML patients.

This Example demonstrates that: 1) DHT formation is important in the protective mechanism of female recipients; 2) finasteride reduces the most potent endogenous ligand (DHT) of AR, which supports the described approach as a therapeutic choice for male AML patients with adjustment of the treatment term due to the persistent generation of endogenous AR ligand in male recipients.

Example 11

The results of this Example are presented in the indicated panels of FIG. 11, and show that an in vivo combination of ARN509 and finasteride decreases the severity of AML in male mice transplanted with female AML donor cells.

The examples above indicated that endogenous DHT is pivotal for AR activation in male recipients. Therefore, targeted 5-α reductase by finasteride and AR by ARN509 in male recipients transplanted with female AML donor cells were treated with a combination treatment schedule.

Figure 11A:
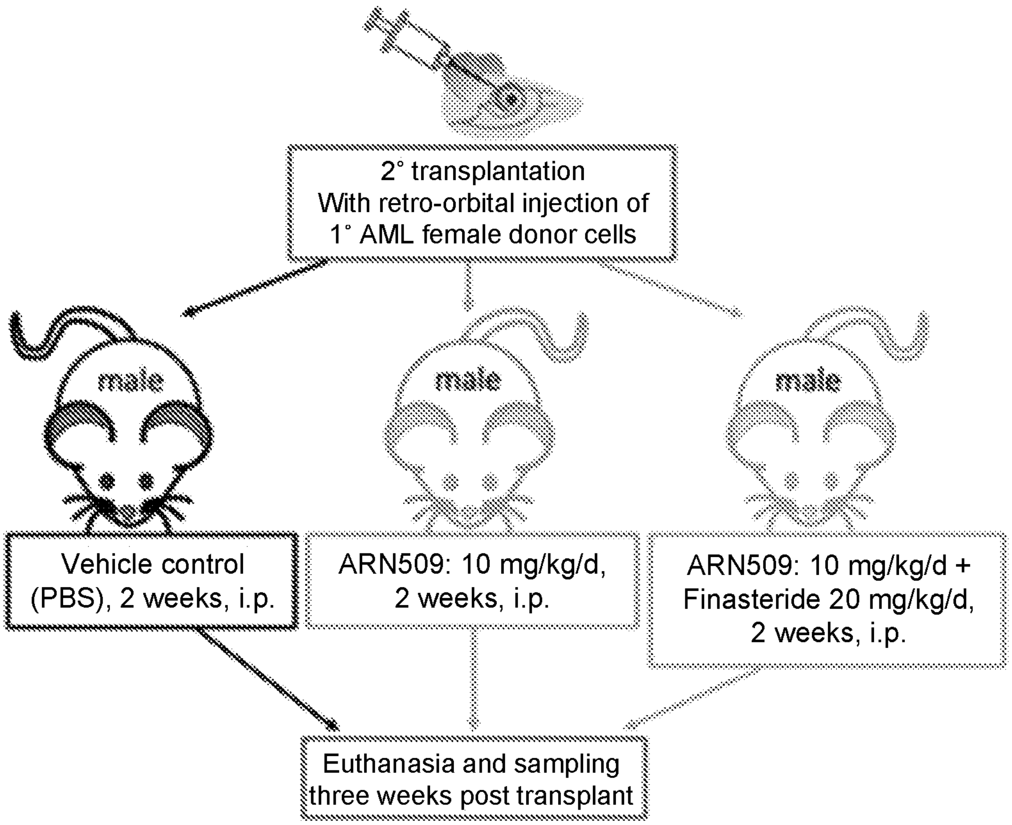
FIG. 11A, FIG. 11B, FIG. 11C, FIG. 11D, FIG. 11E, FIG. 11F, FIG. 11G, FIG. 11H, and FIG. 11I demonstrate in vivo that a combination of ARN509 and finasteride decreases the severity of AML in male mice transplanted with female AML donor cells.
Figure 11B:
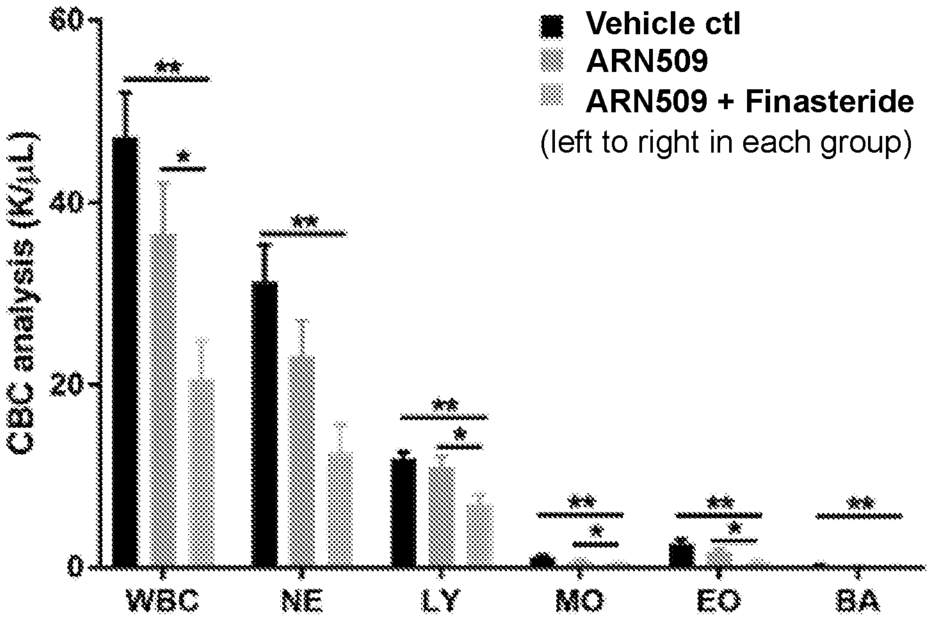
Figure 11C:
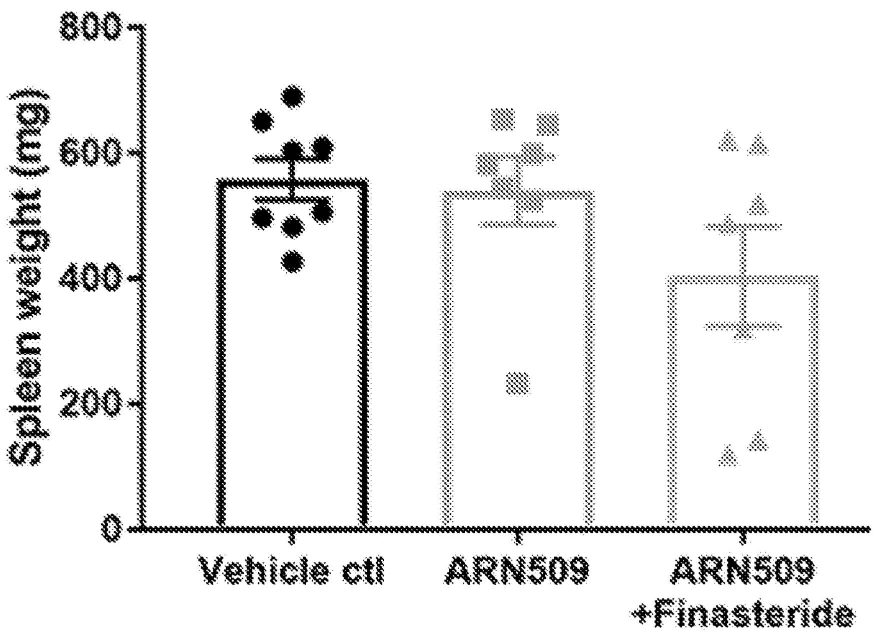
Figure 11D:
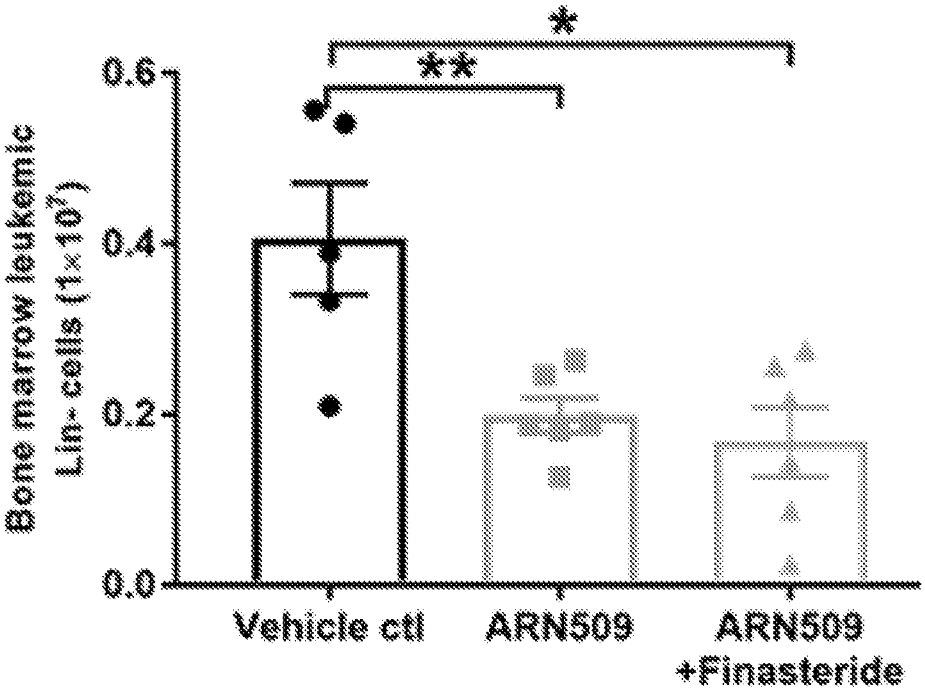
Figure 11E:
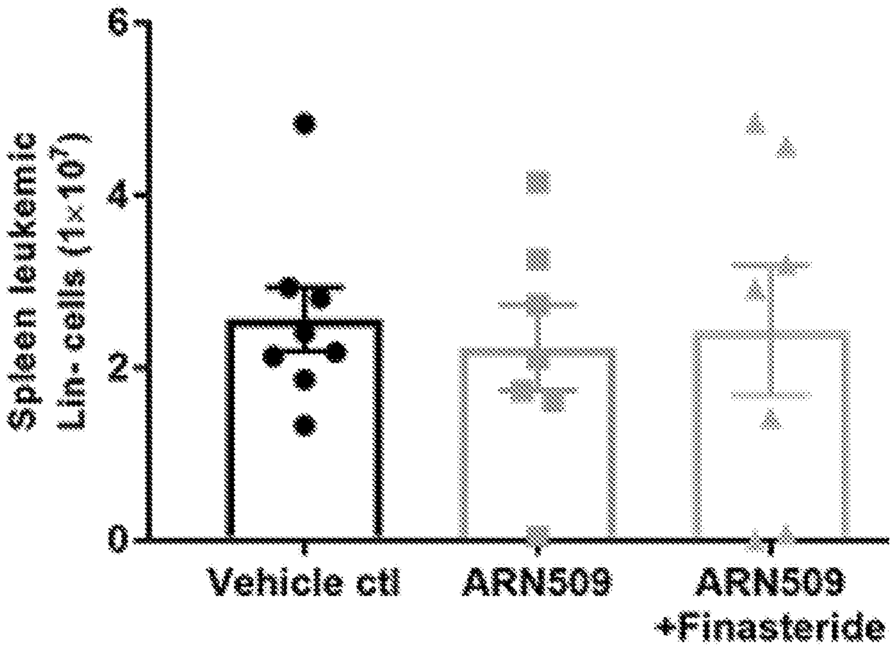
Figure 11F:
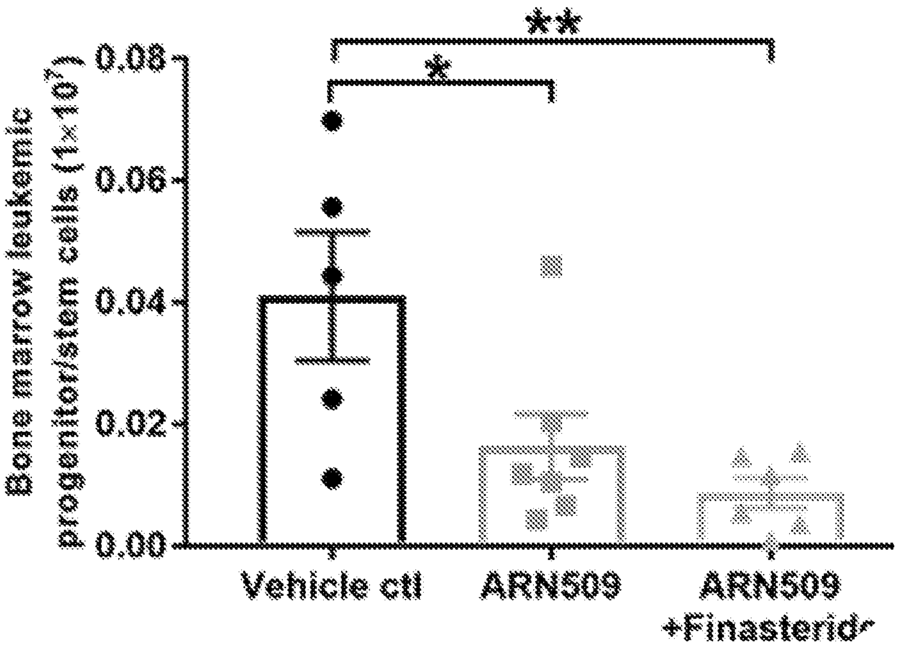
Figure 11G:
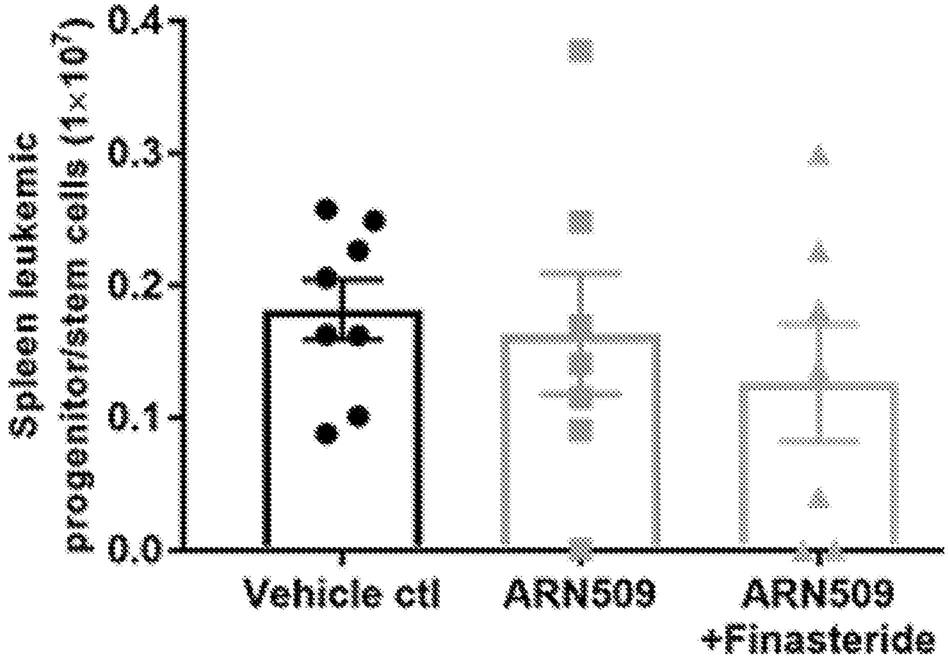
Figure 11H:
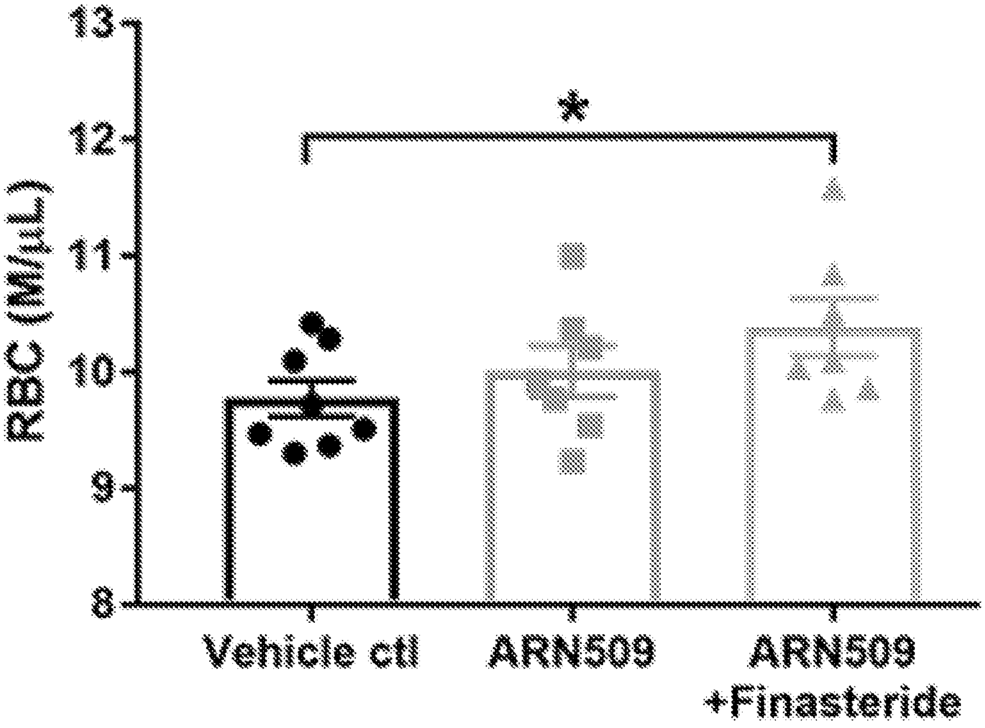
Figure 11I:
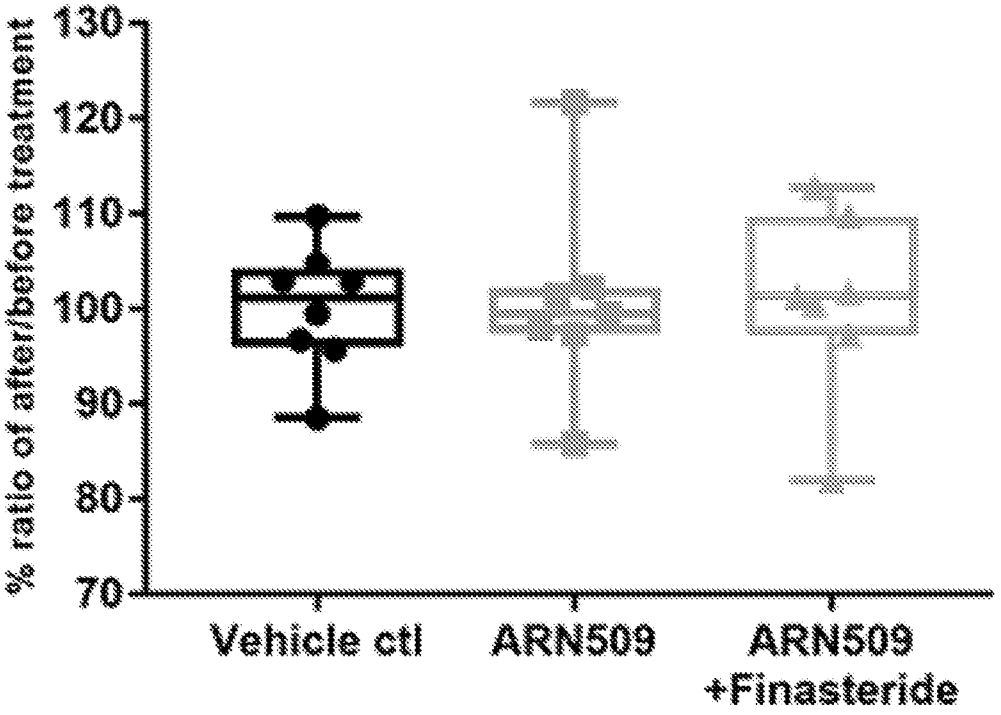

(FIG. 11A) At one week post 2° transplantation of female AML donors into male recipients, the mice were treated with vehicle (PBS), ARN509 (10 mg/kg/d, i.p. injection), or combination of ARN509 (10 mg/kg/d, i.p. injection) and finasteride (20 mg/kg/d, i.p. injection), for two weeks. We found that single ARN509 (10 mg/kg/d) was not able to induce significant anti-leukemic effect; while the addition of finasteride to ARN509 could alleviate the disease by improving leukocytosis (FIG. 11B) and splenomegaly (FIG. 11C) in AML male recipients. The combination treatment significantly reduced the leukemic burden in the bone marrow shown as decreased $Lin^-$ leukemic cells (FIG. 11D) and LICs (FIG. 11F), but not in the spleen (FIG. 11E and FIG. 11 G). On the other hand, the combination treatment also increased the red blood cell counts (FIG. 11H) and did not lead to any changes in body weight (FIG. 11I) suggesting it was tolerated well. In combination the FIG. 6 panels, this Example indicates that antagonism of AR on female AML cells is not sufficient to effectively treat the disease, particularly when the endogenous ligand levels are high (as in male recipients). The data also indicates that additional therapy with finasteride to reduce endogenous DHT production is an effective regimen in successfully treating AML.

Example 12

The results of this Example are presented in FIG. 12 panels, which show survival analysis of the effect of active androgen production in female mice transplanted with female AML donor cells.

Although it is demonstrated above that reduced levels of DHT (FIG. 8B) in female recipients serves as a protective mechanism against AML, we explored if finasteride can be a therapeutic choice for female recipients by further reducing the levels of DHT. To mirror the patient scenario, we performed the experiment on female recipients transplanted with female AML donor cells.

Figure 12A:
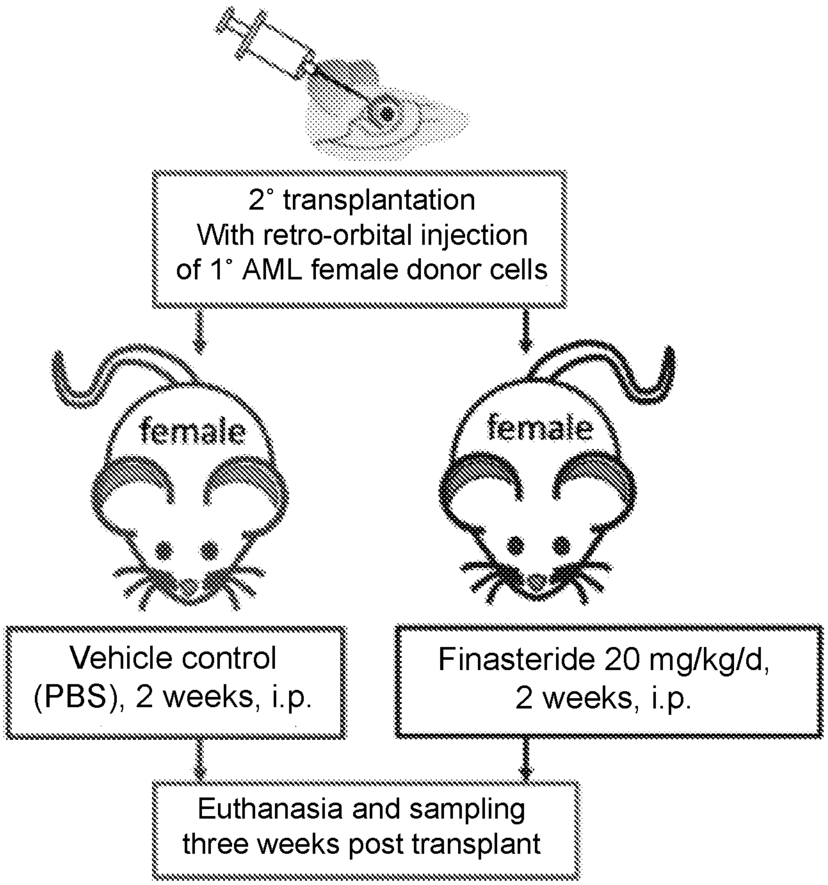
FIG. 12A, FIG. 12B, FIG. 12C, FIG. 12D, FIG. 12E, FIG. 12F, FIG. 12G, FIG. 12H, FIG. 12I, FIG. 12J, and FIG. 12K show survival analysis of the effect of active androgen production in female mice transplanted with female AML donor cells.
Figure 12B:
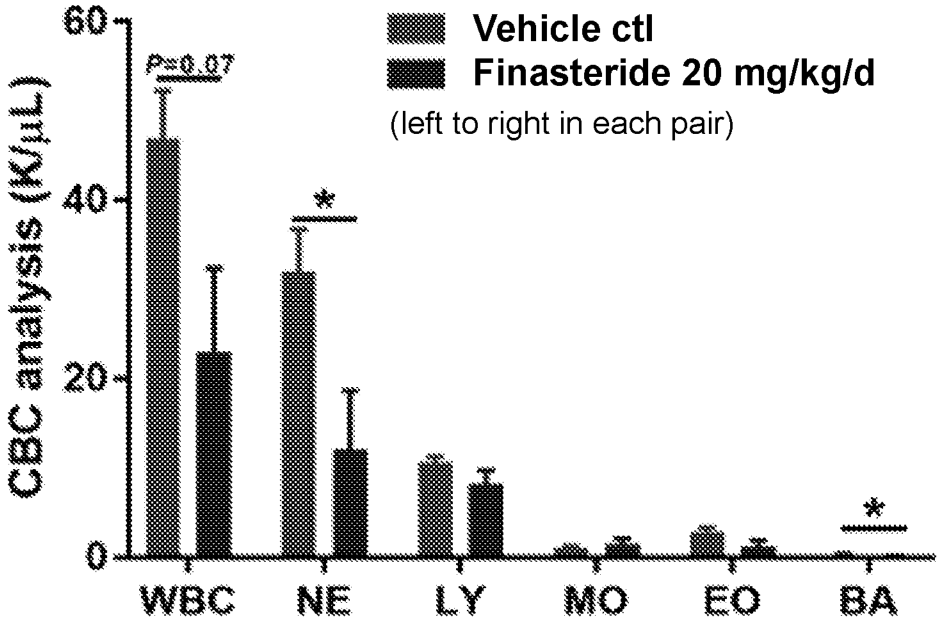
Figure 12C:
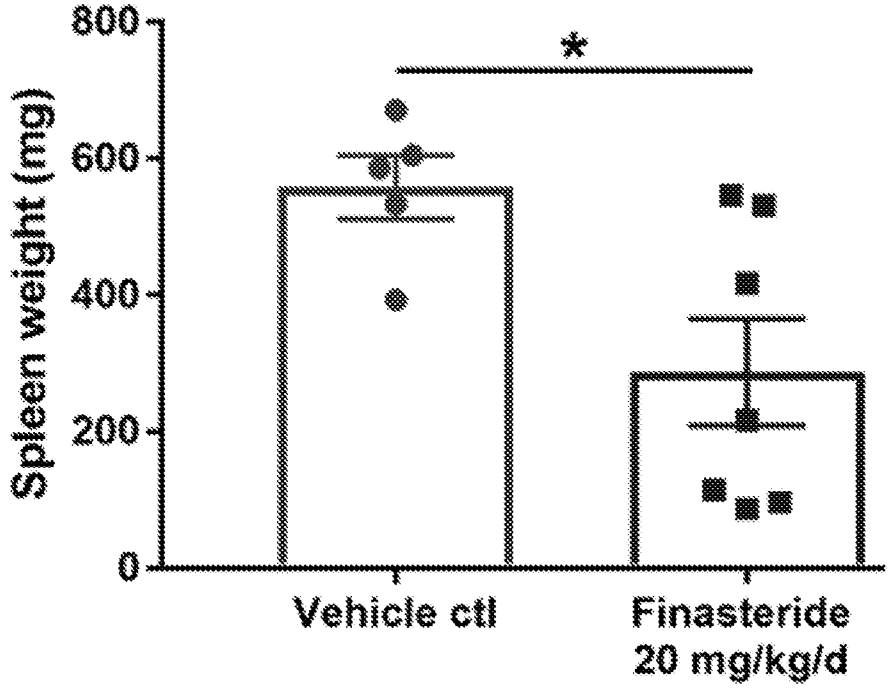
Figure 12D:
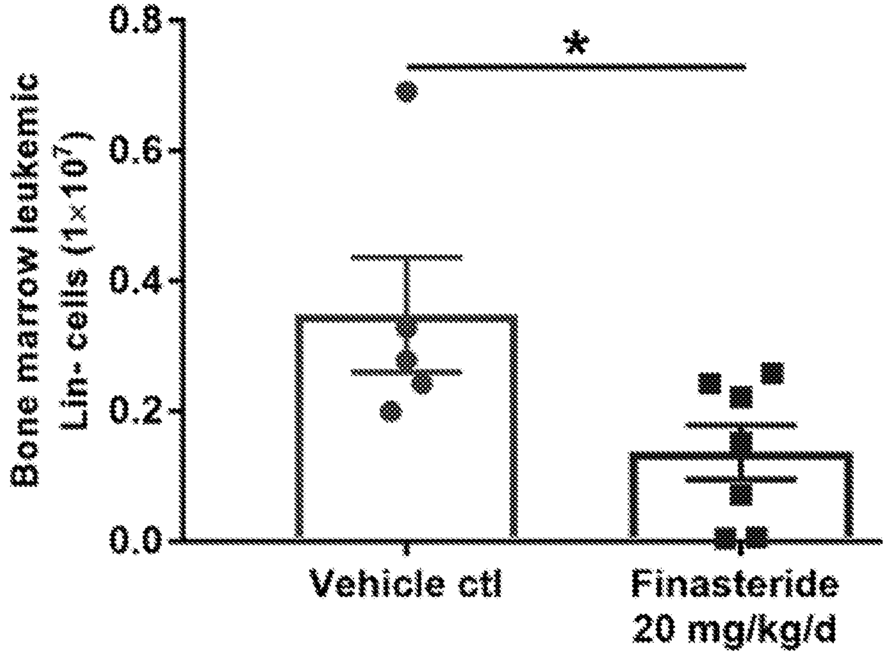
Figure 12E:
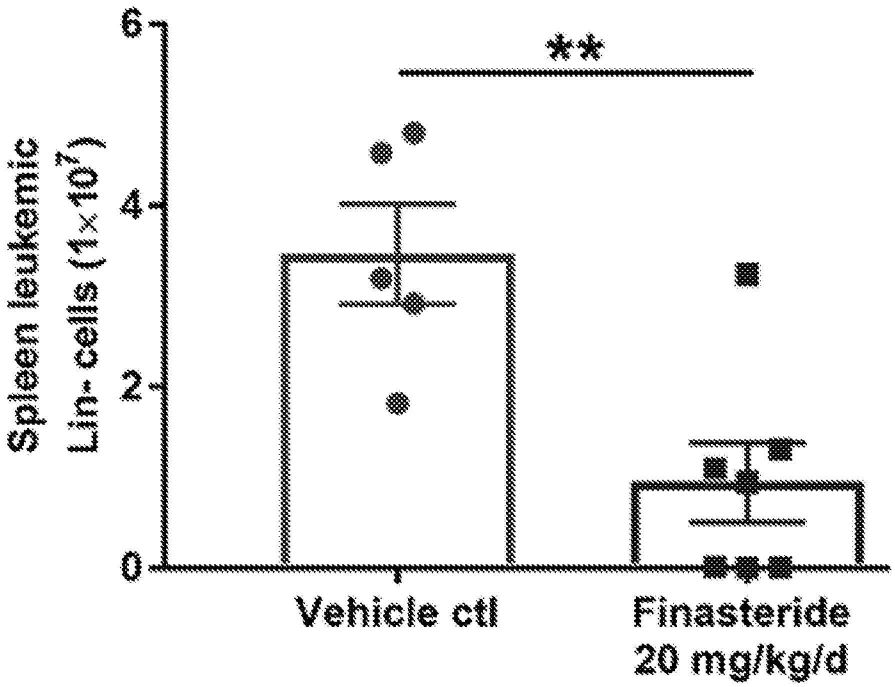
Figure 12F:
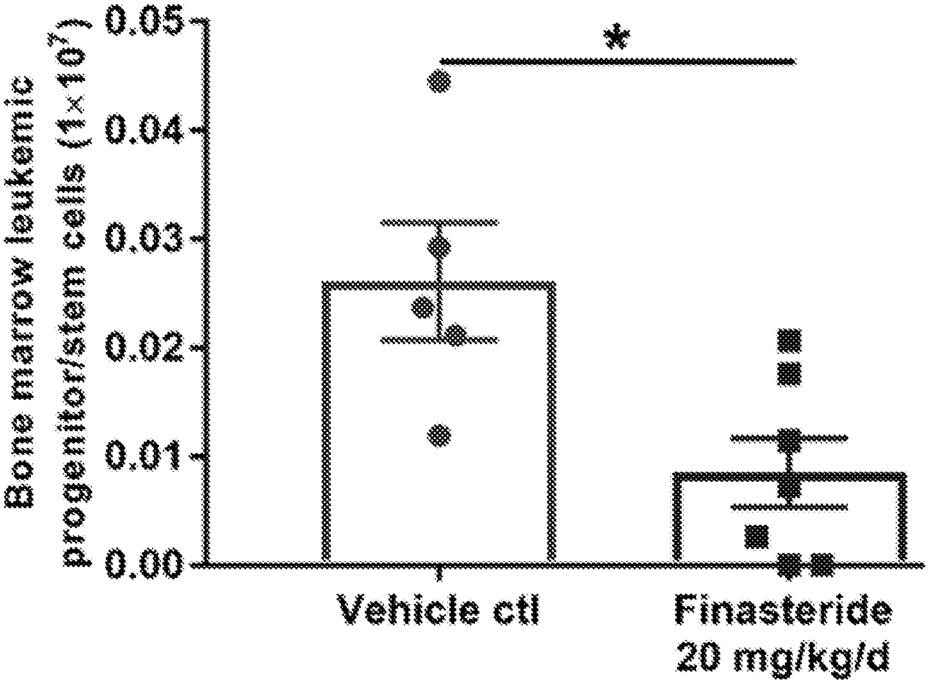
Figure 12G:
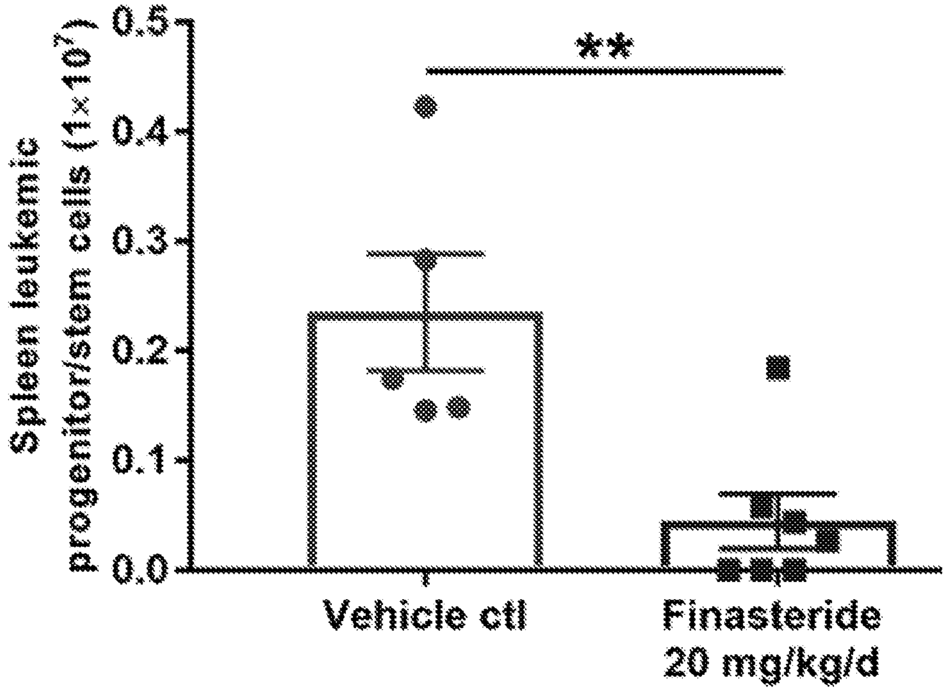
Figure 12H:
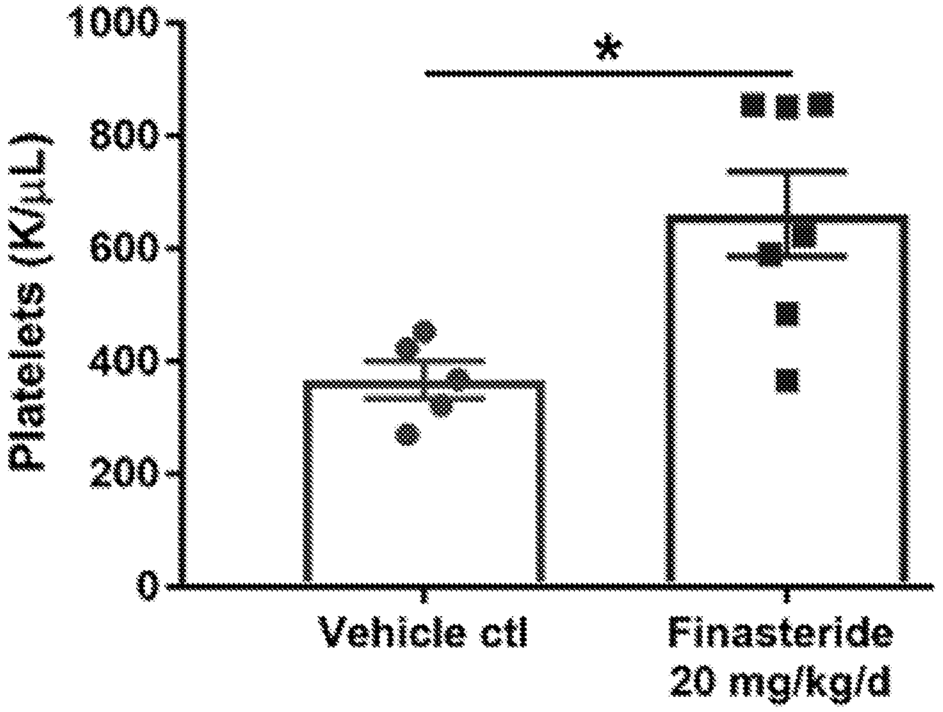
Figure 12I:
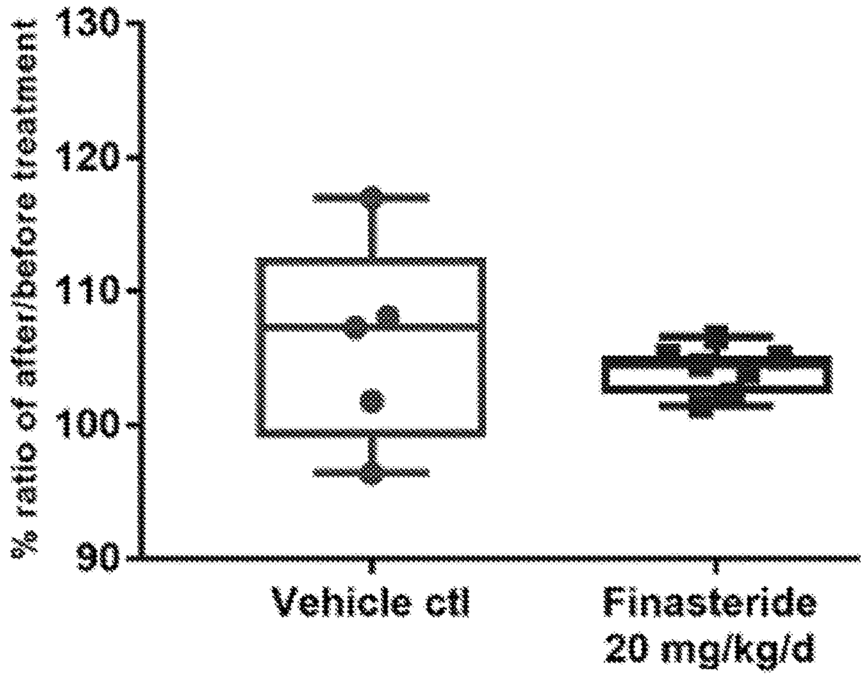
Figure 12J:
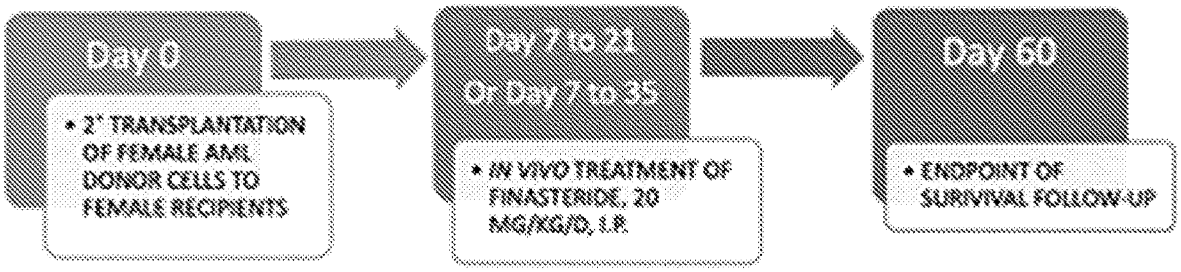
Figure 12K:
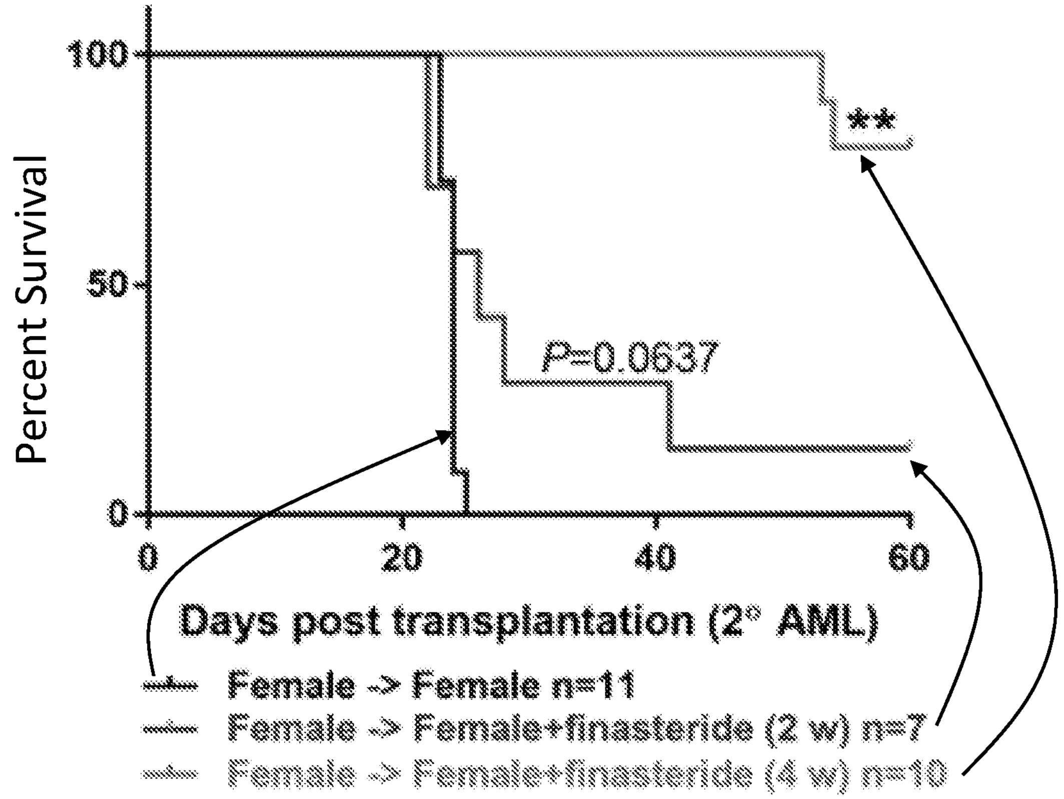

(FIG. 12A) At one week after 2° transplantation of female AML donors to female recipients, we treated the mice with vehicle (PBS) or finasteride (20 mg/kg/d, i.p. injection) for two weeks. Even in female recipients who have limited DHT generation, finasteride could still significantly improve leukocytosis (FIG. 12B) and splenomegaly (FIG. 12C). Finasteride also significantly reduced the leukemic burden in the bone marrow and spleen shown as decreased $Lin^-$ leukemic cells (FIG. 12D and FIG. 12F) and LICs (FIG. 12E and FIG. 12G). Moreover, the therapeutic effect of in vivo finasteride treatment (FIG. 12J) benefitted the survival of female recipients transplanted with female AML donors (FIG. 12K), but the prospect of long-term treatment needs to be evaluated.

These data indicate that finasteride can also be a treatment for female AML patients even though female patients may not produce DHT as high as male recipients. The disclosure includes long-term treatment of finasteride to persistently inhibit the activation of AR on AML cells.

The foregoing examples are intended to illustrate embodiments of the disclosure but are not intended to be limiting.

What is claimed is:

1. A method for treating a blood cancer in an individual in need thereof, the method comprising administering to the individual:

i) an agent that inhibits activity or expression of one or more enzymes that participate in synthesis of either or both dihydrotestosterone (DHT) or androgen receptor (AR), or ii) an antagonist AR, or a combination of agents of i) and ii).

2. The method of claim 1, wherein the blood cancer comprises acute myeloid leukemia (AML).

3. The method of claim 2, wherein the agent that inhibits the one or more enzymes that participate in synthesis of the DHT inhibits 5-α reductase.

4. The method of claim 3, wherein the agent that inhibits the 5-α reductase is administered, and wherein said agent comprises finasteride.

5. The method of claim 1, wherein the antagonist of the AR is administered.

6. The method of claim 5, wherein the antagonist of the AR comprises ARN-509.

7. The method of claim 2, wherein a combination of an agent that inhibits the 5-α reductase and the antagonist of the AR is administered.

8. The method of claim 7, wherein the combination comprises finasteride and ARN-509.

9. The method of claim 8, wherein the individual who has the blood cancer does not have prostate cancer, and wherein the blood cancer is AML.

10. The method of claim 1, wherein the individual does not have prostate cancer.

11. The method of claim 1, wherein the individual is a female human.

* * * * *